United States Patent
Kiely et al.

(10) Patent No.: US 11,845,680 B2
(45) Date of Patent: *Dec. 19, 2023

(54) BIO-ELECTROCHEMICAL SENSOR, SYSTEM AND METHOD FOR MONITORING AND CONTROLLING ORGANIC CARBON LEVELS IN A WASTEWATER TREATMENT PROCESS

(71) Applicant: SENTRY: WATER MONITORING AND CONTROL INC., Charlottetown (CA)

(72) Inventors: Patrick Desmond Kiely, Gatineau (CA); Jack R. Ambler, Conshohocken, PA (US); Colin Ragush, Halifax (CA)

(73) Assignee: SENTRY: WATER MONITORING AND CONTROL INC., Charlottetown (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/645,082

(22) PCT Filed: Sep. 7, 2018

(86) PCT No.: PCT/CA2018/051102
§ 371 (c)(1),
(2) Date: Mar. 6, 2020

(87) PCT Pub. No.: WO2019/046963
PCT Pub. Date: Mar. 14, 2019

(65) Prior Publication Data
US 2020/0283314 A1    Sep. 10, 2020

Related U.S. Application Data

(60) Provisional application No. 62/555,290, filed on Sep. 7, 2017.

(51) Int. Cl.
*C02F 3/00* (2023.01)
*C02F 3/30* (2023.01)
(Continued)

(52) U.S. Cl.
CPC .............. *C02F 3/006* (2013.01); *C02F 3/308* (2013.01); *C12Q 1/02* (2013.01); *G01N 27/327* (2013.01);
(Continued)

(58) Field of Classification Search
CPC ...... C02F 3/006; C02F 3/308; C02F 2209/12; C02F 2209/36; C02F 2305/06;
(Continued)

(56) References Cited

U.S. PATENT DOCUMENTS 5,288,406 A * 2/1994 Stein ...................... C02F 3/302
                                                              210/614
5,482,630 A * 1/1996 Lee ........................... C02F 3/28
                                                              210/903
(Continued)

FOREIGN PATENT DOCUMENTS

WO    WO-0104626 A1 * 1/2001 ......... G01N 33/1866
WO    WO-2010147683 A1 * 12/2010 .............. C02F 3/303
(Continued)

OTHER PUBLICATIONS

International Patent Application No. PCT/CA2018/051102, International Preliminary Report on Patentability dated Mar. 19, 2020.
(Continued)

*Primary Examiner* — Ekandra S. Miller-Cruz
(74) *Attorney, Agent, or Firm* — Borden Ladner Gervais LLP; Michael Damiani

(57) ABSTRACT

The present disclosure generally relates to a system for monitoring and/or controlling the delivery of one or more organic carbon compounds to a wastewater treatment sys-
(Continued)

tem. The system comprises a bio-electrochemical sensor to monitor metabolic activity of a population of exo-electrogenic bacteria and provide an electrical output corresponding with the metabolic activity, the bio-electrochemical sensor comprising an electrode pair and a power source to deliver a voltage across the electrode pair, and an electrical output analyzer to analyze the electrical output and correlate the electrical output with a value representing the amount of the one or more organic carbon compounds in the wastewater treatment system. A method and sensor for monitoring and/or controlling the delivery of one or more organic carbon compounds to a wastewater treatment system are also provided.

12 Claims, 11 Drawing Sheets

(51) Int. Cl.
C12Q 1/02 (2006.01)
G01N 27/327 (2006.01)
G01N 33/92 (2006.01)

(52) U.S. Cl.
CPC .......... *G01N 33/92* (2013.01); *C02F 2209/12* (2013.01); *C02F 2209/36* (2013.01); *C02F 2305/06* (2013.01); *G01N 2405/00* (2013.01)

(58) Field of Classification Search
CPC .. C02F 3/305; C12Q 1/02; C12Q 1/04; G01N 27/327; G01N 33/92; G01N 2405/00; G01N 33/1806; G01N 33/18; C12M 1/34; C12M 1/36

USPC .................................. 210/606, 610, 666, 698
See application file for complete search history.

(56) References Cited

U.S. PATENT DOCUMENTS

| | | |
|---|---|---|
| 9,475,714 B2 * | 10/2016 | Amir ...................... C02F 3/006 |
| 11,352,272 B2 | 6/2022 | Kiely et al. |
| 2002/0052016 A1 | 5/2002 | Dragotta et al. |
| 2014/0353170 A1 | 12/2014 | Huang et al. |
| 2016/0272519 A1 | 9/2016 | Ledwell et al. |
| 2021/0214251 A1 | 7/2021 | Ragush et al. |

FOREIGN PATENT DOCUMENTS

| | | |
|---|---|---|
| WO | 2012012647 A2 | 1/2012 |
| WO | 2014172791 A1 | 10/2014 |
| WO | 2018094537 A1 | 5/2018 |

OTHER PUBLICATIONS

International Patent Application No. PCT/CA2018/051102, International Search Report and Written Opinion dated Dec. 7, 2018.
European Patent Application No. 18854118.9, Communication pursuant to Article 94(3) EPC dated Nov. 26, 2021.
European Patent Application No. 18854118.9, Extended European Search Report dated May 11, 2021.
European Patent Application No. 18854118.9, European Office Action dated Jan. 4, 2023.

* cited by examiner

BIO-ELECTROCHEMICAL SENSOR, SYSTEM AND METHOD FOR MONITORING AND CONTROLLING ORGANIC CARBON LEVELS IN A WASTEWATER TREATMENT PROCESS

FIELD

The present disclosure relates generally to a bio-electrochemical sensor for monitoring the metabolic activity of exo-electrogenic microbial populations in a wastewater treatment process, and systems and methods related thereto.

BACKGROUND

The necessity of cost-efficient and reliable waste water treatment processes has increased in order to meet more stringent levels of environmental regulations, increased system reliability requirements and to allow operators to reduce costs associated with system operation and maintenance. The discharge of wastewater requires control of the quantity and concentration of certain inorganic nutrients, for example nitrogen and phosphorous, that are released to the environment.

Nitrogen Removal

Nitrogen removal in a wastewater treatment context encompasses converting fixed nitrogen (e.g. ammonia) into nitrogen gas that can be released from the wastewater treatment process. In a wastewater treatment plant, this process typically occurs through two key steps, nitrification and denitrification. The challenge for operators of wastewater treatment facilities is that, for nitrification to occur, the wastewater has to have very low concentrations of available carbon (e.g. COD, BOD or volatile fatty acids). The second step, however, requires that same carbon to be present to complete the denitrification step. Facultative anaerobic bacteria perform denitrification as a type of respiration that reduces oxidized forms of nitrogen in response to the oxidation of an electron donor such as organic matter. These bacteria therefore require a carbon source to perform denitrification. This requirement has led to a process where wastewater treatment facilities dose supplemental carbon into wastewater treatment facilities to allow for denitrification and nitrogen removal from the wastewater stream. This can be performed in continuous feed process designs and sequencing batch reactors (batch). Examples of methods used for nitrogen removal include: step feeding, oxidation ditches, sequencing batch reactors (SBRs), and membrane aerated biofilm reactors (MABRs), which are described briefly below.

Step feeding entails diverting a portion of an influent into anoxic tanks to provide carbon from the influent for the denitrification step. This can be achieved in both typical continuous flow and batch type designs.

Use of oxidation ditches that have a large recycle allow a wastewater treatment plant to change the location and dimensions of their aeration/anoxic/anaerobic steps by controlling aeration location and quantity as well as recycle rates. This can be achieved by utilizing specific on/off timing for aeration, as well as moving aerators. Ditches can use this ability with the potential shifting location of the influent relative to the tanks to complete a nitrogen cycle.

Sequencing Batch Reactors (SBRs) can achieve nitrogen removal by offsetting their "on" and "off" times, and moving liquid between SBRs during precise times to provide the required environment for removal (nitrification and denitrification). The denitrification can be achieved using endogenous decay, using the activated sludge or microorganism population is the carbon source for denitrification.

Membrane Aerated Biofilm Reactors (MABRs) use passive diffusion of oxygen through a membrane into a biofilm. This process maintains a dissolved oxygen concentration in the reactor as negligible and allows for nitrification and denitrification to take place in the same reactor, or in the same biofilm. Nitrification and denitrification can be designed to occur at the same time in a wastewater process. This requires specific sludge control, and specific dissolved oxygen (D.O.) control amongst additional factors. This can be done with a single sludge return or separate sludge return.

For all of the above examples of methods used for nitrogen removal, depending on what effluent concentrations are desired, the number of reactors and specific order of tanks can be modified to achieve greater effluent results.

A wide range of carbon sources (supplemental carbon) can be used to meet the denitrification requirements. Examples include methanol, ethanol, acetate, acetic acid, glycerol, molasses sugar water, or MicroC™. Choice of a carbon source can depend on a number of factors that include cost, safety and performance. Dosage requirements refer to an amount of COD that is required to remove each nit of nitrate (e.g. COD:N ratio). This ratio can be impacted greatly depending on the type of carbon source used, species of microbes present, solids retention time and sludge yields of microbial populations.

One of the key challenges for nitrogen removal is controlling the dosing of carbon to the system so as to provide sufficient rates of nitrification and/or denitrification and simultaneously saving costs by not over dosing systems with carbon.

Phosphorous Removal

Regulatory restrictions continue to be tightened on phosphorous effluent from wastewater treatment plants. One process of removing phosphorous from wastewater is Enhanced Biological Phosphorous Removal (EBPR). EBPR is a nutrient removal strategy that incorporates an anaerobic chamber positioned upstream from an aerobic chamber. This process is used to enrich or select for a group of heterotrophic bacteria called polyphosphate-accumulating organisms (PAO). This microbial population accumulates large quantities of polyphosphate within their cells allowing for removal of phosphorous from a solution. PAO populations consume phosphorous for cellular components but more importantly accumulate large quantities within their cells (5-7% of biomass). This biomass can then be separated from wastewater thereby removing the phosphorous.

Uptake of phosphorous occurs under aerobic conditions. The PAOs however must first be conditioned by exposure to food under anaerobic conditions. PAOs store the food under anaerobic conditions and then process the stored food once under aerobic conditions. The preferred foods for PAOs are volatile fatty acids (VFA), e.g. acetic, propionic, and butyric acids. A key step is to expose PAOs to a sufficient amount of food, thereby depleting their energy reserves causing the PAOs to go into a stress response. This stress response results in PAO communities that rapidly accumulate phosphorous in their cells. The trigger for this phosphorous uptake is subsequent aeration, however the level to which the phosphorous is accumulated is proportional to the stress response. Once the PAO have taken up phosphorous, they are settled out of the solution and removed from the wastewater. If the PAOs are exposed to unfavorable conditions, for example insufficient aeration in an aeration chamber, the PAOs may release the phosphorous from their cells. If this release is triggered while they are still in the wastewater process, the released phosphorous will not be treated and discharged, which can result in a host of environmental issues downstream of a wastewater treatment plant as well as monetary fines and other punitive actions.

EBPR requires sufficient VFA concentrations in the anaerobic step in order for the process to properly select for PAOs. Fermentation can occur in multiple locations and depends heavily on the collection system and the influent wastewater. VFA concentrations can be produced in an anaerobic step in the wastewater process, changing the onsite clarifiers, sludge thickeners, digesters, and other tanks on site into anaerobic steps with the appropriate retention time. It can also be done by activating a collection system. This is done by making a collection system anaerobic where possible and potentially adding chemicals in the system to avoid hydrogen sulfide generation. This can bring additional VFA into the wastewater process system.

It was originally thought that adjusting VFAs present to a proper minimum concentration was sufficient. At this minimum concentration, one microbe group could produce the required VFAs and the PAO organisms would uptake them (i.e. as carbon storage). Thus, two distinct populations were needed to be selected for and accommodated. It has since been found that increasing VFA concentration further than the minimum (with increased levels of fermentation), and by proxy decreasing the oxidation-reduction potential (ORP) values of the wastewater further, it is possible to select for more favorable PAO organisms (i.e. Tetrasphaera).

One of the key challenges for EBPR is controlling the quantity of available food in proportion to the amount of phosphorous to be removed in the anaerobic chamber so as to provide sufficient PAO activity in the aerobic chamber.

There exists a need for improved monitoring and control of organic carbon compound concentrations, for example VFA concentration, in a wastewater treatment process.

INTRODUCTION

The following introduction is intended to introduce the reader to this specification but not to define any invention. One or more inventions may reside in a combination or sub-combination of the apparatus or system elements or method steps described below or in other parts of this document. The inventors do not waive or disclaim their rights to any invention or inventions disclosed in this specification merely by not describing such other invention or inventions in the claims.

Bio-electrochemical sensors (BES) are relatively new technology that rely on bacteria that normally use insoluble metal deposits as electron sinks during anaerobic consumption of reduced substrates. By substituting an electrode for the metal deposits, electrical current can be collected or recorded as it passes through an external resistor. The metabolic activity and respective bioelectric current of these BES systems has been identified to vary according to wide ranging environmental alterations that include, water composition/chemistry (nutrient content, pH, redox state), temperature and recirculation/sheer.

In a denitrification process, the denitrifying bioreactor may contain low amounts of organic carbon, high amounts of nitrate, and trace amount of oxygen, in solution. Similarly, during the conditioning step of POAs during EBPR, the bioreactor may contain low amount of organic carbon and trace amounts of oxygen, in solution. In such denitrification and EBPR environments, a skilled person would not consider to use a BES because: (1) the presence of nitrate and/or oxygen may inhibit the microbial population of BES from donating elements to the electrode surface of the BES by, for example, competing as an electron acceptor; (2) the low amounts of organic carbon, and thereby an electron source, may provide insufficient resolution of the BES signal; or (3) a combination thereof.

Surprisingly, the present inventors have discovered that BES comprising an electrode pair and a power source to deliver a voltage across the electrode pair, that monitor metabolic activity of a population of exo-electrogenic bacteria and provide an electrical output corresponding with the metabolic activity, may be used in wastewater treatment environments containing low amounts of organic carbon, high amounts of nitrate, and/or trace amounts of oxygen, and provide sufficient signal resolution to monitor and/or control the amount of one or more organic compounds in the bioreactor environments during nitrogen removal and/or phosphorous removal processes.

One or more examples according to the present disclosure may: (1) increase accuracy of measurement; (2) increase efficiency of nitrogen removal and/or phosphorous removal processes; (3) reduce operation costs; (4) increase efficiency and/or performance of a wastewater treatment system; (5) improve timing of batch cycle operation and increase efficiency of switching between batch modes of operation based on BES output; or (6) a combination thereof, in comparison to one or more systems, methods, and sensors previously disclosed, by, for example: (1) enhancing monitoring and/or controlling the delivery of one or more organic carbon compounds in bioreactor environments that contain low amounts of organic carbon, high amounts of nitrate, and/or trace amount of oxygen, in solution (2) reducing overdosing of organic carbon compounds; (3) decreasing the downtime of wastewater treatment systems by adjusting the amount, type, or combination thereof, of organic carbon compounds delivered into the wastewater treatment system; or (4) a combination thereof.

In one aspect, the present disclosure provides for a system for monitoring one or more organic carbon compounds in a wastewater treatment system. The system comprises: a bio-electrochemical sensor to monitor metabolic activity of a population of exo-electrogenic bacteria and provide an electrical output corresponding with the metabolic activity, the bio-electrochemical sensor comprising an electrode pair and a power source to deliver a voltage across the electrode pair; and an electrical output analyzer to analyze the electrical output and correlate the electrical output with a value representing the amount of the one or more organic carbon compounds in the wastewater treatment system.

The wastewater treatment system may be an anaerobic or anoxic digestion system, and the bio-electrochemical sensor may be located within the anaerobic or anoxic digestion system. The anoxic or anaerobic digestion system may be a denitrifying tank. The anoxic or anaerobic digestion system may be an anaerobic phosphorous removal tank. The anoxic or anaerobic digestion system may comprise nitrate at a concentration from about 5 mg/L to about 100 mg/L, bio-available carbon at a concentration from 0 mg/L to about 100 mg/L, oxygen at a concentration of about ≤2 mg/L, or a combination thereof.

The one or more organic carbon compounds may comprise a volatile fatty acid, an organic acid, or a complex organic compound. The one or more organic carbon compounds may comprise a volatile fatty acid. The volatile fatty acid may be acetic acid, propionic acid, butyric acids, or a combination thereof.

In another aspect, the present disclosure provides a system for controlling the delivery of one or more organic carbon compounds to a wastewater treatment system. The system comprises: a bio-electrochemical sensor to monitor metabolic activity of a population of exo-electrogenic bacteria and provide an electrical output correlating with the metabolic activity, the bio-electrochemical sensor comprising an electrode pair and a power source to deliver a voltage across the electrode pair; an electrical output analyzer to analyze the electrical output and correlate the electrical output with a value representing the amount of the one or more organic carbon compounds in the wastewater treatment system, and provide a signal to a controller; and a pump operably coupled to the controller to control the delivery of the one or more organic carbon compounds in response to the signal.

The wastewater treatment system may be an anaerobic or anoxic digestion system, and the bio-electrochemical sensor may be located within the anaerobic or anoxic digestion system. The anoxic or anaerobic digestion system may be a denitrifying tank. The anoxic or anaerobic digestion system may be an anaerobic phosphorous removal tank. The anoxic or anaerobic digestion system may comprise nitrate at a concentration from about 5 mg/L to about 100 mg/L, bio-available carbon at a concentration from 0 mg/L to about 100 mg/L, oxygen at a concentration of about ≤2 mg/L, or a combination thereof.

The one or more organic carbon compounds may comprise a volatile fatty acid, an organic acid, or a complex organic compound. The one or more organic carbon compounds may comprise a volatile fatty acid. The volatile fatty acid may be acetic acid, propionic acid, butyric acids, or a combination thereof.

The system may permit real time adjustments in the delivery of the one or more organic carbon compounds.

A change in electrical output beyond a threshold may produce a signal to adjust the delivery of the one or more organic carbon compounds. The threshold may be a deviation of greater than about 10% from an operating electrical output. The threshold may represent a change in a ratio of the value representing the amount of one or more organic carbon compounds to a value representing the amount of nitrogen in the system. The delivery of the one or more organic carbon compounds may initiate, adjust, maintain, or stop a nitrification process. The delivery of the one or more organic carbon compounds may initiate, adjust, maintain, or stop a simultaneous nitrification and denitrification process. The ratio may be about 0:1; about 1:1; about 2:1; about 3:1; about 4:1; about 5:1; about 6:1; about 7:1; about 8:1; about 9:1; or about 10:1. The delivery of the one or more organic carbon compounds may initiate, adjust, maintain, or stop a denitrification process. The ratio may be greater than about 4:1; greater than about 5:1; greater than about 6:1; greater than about 7:1; greater than about 8:1; greater than about 9:1; greater than about 10:1; greater than about 11:1; or greater than about 12:1.

The threshold may represent a change in a ratio of the value representing the amount of one or more organic carbon compounds to a value representing the amount of phosphorous in the system. The delivery of the one or more organic carbon compounds may initiate, adjust, maintain, or stop a carbon addition of a phosphorous removal process. The ratio may be less than about 10:1; less than about 15:1; less than about 20:1; less than about 25:1; less than about 30:1; less than about 35:1; less than about 40:1; less than about 45:1; or less than about 50:1.

The change in electrical output may be monitored over a period of time.

The electrode pair may comprise an anode and a cathode, the anode in electrical communication with the exo-electrogenic bacteria for receiving electrons therefrom, and the bio-electrochemical sensor may further comprise a current sensor for measuring electron flow between the anode and the cathode and producing an electrical output that correlates with metabolic activity of the exo-electrogenic bacteria. The current sensor may comprise a terminal electron acceptor in electrical communication with the cathode for receiving electrons therefrom, and a resistor in electrical communication with the terminal electron acceptor, wherein an electric current is measured across the resistor. The terminal electron accepter may be a non-oxygen electron acceptor. The non-oxygen electron acceptor may be H+ or $CO_2$.

In another aspect, the present disclosure provides a method of monitoring one or more organic carbon compounds in a wastewater treatment system. The method comprises: applying power to a bio-electrochemical sensor; measuring an electrical output of the bio-electrochemical sensor and correlating the output with metabolic activity of exo-electrogenic bacteria present in the system; and correlating the electrical output with the one or more organic carbon compounds in the wastewater treatment system.

The wastewater treatment system may be an anaerobic or anoxic digestion system, and the bio-electrochemical sensor may be located within the anaerobic or anoxic digestion system. The anoxic or anaerobic digestion system may be a denitrifying tank. The anoxic or anaerobic digestion system may be an anaerobic phosphorous removal tank. The anoxic or anaerobic digestion system may comprise nitrate at a concentration from about 5 mg/L to about 100 mg/L, bio-available carbon at a concentration from 0 mg/L to about 100 mg/L, oxygen at a concentration of about ≤2 mg/L, or a combination thereof.

The one or more organic carbon compounds may comprise a volatile fatty acid, an organic acid, or a complex organic compound. The one or more organic carbon compounds may comprise a volatile fatty acid. The volatile fatty acid may be acetic acid, propionic acid, butyric acids, or a combination thereof.

In another aspect, the present disclosure provides a method of controlling the delivery of one or more organic carbon compounds in a wastewater treatment system. The method comprises: applying power to a bio-electrochemical sensor; measuring an electrical output of the bio-electrochemical sensor and correlating the output with metabolic activity of exo-electrogenic bacteria present in the system; delivering the one or more organic carbon compounds into the system; monitoring a change in the electrical output in response to the one or more organic carbon compounds; and adjusting the delivery of the one or more organic carbon compounds in response to a change in the electrical output.

The wastewater treatment system may be an anaerobic or anoxic digestion system, and the step of measuring the electrical output may be measured within the anaerobic or anoxic digestion system. The anoxic or anaerobic digestion system may be a denitrifying tank. The anoxic or anaerobic digestion system may be an anaerobic phosphorous removal tank. The anoxic or anaerobic digestion system may comprise nitrate at a concentration from about 5 mg/L to about 100 mg/L, bio-available carbon at a concentration from 0 mg/L to about 100 mg/L, oxygen at a concentration of about ≤2 mg/L, or a combination thereof.

The one or more organic carbon compounds may comprise a volatile fatty acid, an organic acid, or a complex organic compound. The one or more organic carbon compounds may comprise a volatile fatty acid. The volatile fatty acid may be acetic acid, propionic acid, butyric acids, or a combination thereof.

The adjusting step may comprise real time adjustments in the delivery of the one or more organic carbon compounds.

The delivery of the one or more organic carbon compounds may be adjusted in response to a change in electrical output beyond a threshold. The threshold may be a deviation of greater than about 10% from an operating electrical output. The change in electrical output may be monitored over a period of time.

In another aspect, the present disclosure provides a method of controlling a nitrogen removal process in a wastewater treatment system. The method comprises: applying power to a bio-electrochemical sensor; measuring an electrical output of the bio-electrochemical sensor and correlating the output with a metabolic activity of exo-electrogenic bacteria present in the system; delivering one or more organic carbon compounds into the system; monitoring a change in the electrical output in response to the one or more organic carbon compounds, the electrical output corresponding to a value representing the amount of the one or more organic carbon compounds in the wastewater treatment system; and adjusting the delivery of the one or more organic carbon compounds in response to a change in the electrical output.

The one or more organic carbon compounds may comprise a volatile fatty acid, an organic acid, or a complex organic compound. The one or more organic carbon compounds may comprise a volatile fatty acid. The volatile fatty acid may be acetic acid, propionic acid, butyric acids, or a combination thereof.

The change in electrical output may be monitored over a period of time.

The adjusting step may comprise real time adjustments in the delivery of the one or more organic carbon compounds throughout the nitrogen removal process in response to changes in the electrical output.

The delivery of the one or more organic carbon compounds may be adjusted in response to a change in electrical output beyond a threshold. The threshold may be a deviation of greater than about 10% from an operating electrical output. The threshold may represent a change in a ratio of the value representing the amount of one or more organic carbon compounds to a value representing the amount of nitrogen in the system. The delivery of the one or more organic carbon compounds may initiate, adjust, maintain, or stop nitrification of the nitrogen removal process. The delivery of the one or more organic carbon compounds may initiate, adjust, maintain, or stop simultaneous nitrification and denitrification of the nitrogen removal process. The ratio may be about 0:1; about 1:1, about 2:1; about 3:1; about 4:1; about 5:1; about 6:1; about 7:1; about 8:1; about 9:1; or about 10:1. The delivery of the one or more organic carbon compounds may initiate, adjust, maintain, or stop denitrification process of the nitrogen removal process. The ratio may be greater than about 4:1; greater than about 5:1; greater than about 6:1; greater than about 7:1; greater than about 8:1; greater than about 9:1; greater than about 10:1; greater than about 11:1; or greater than about 12:1.

In another aspect, the present disclosure provides a method of controlling a phosphorous removal process in a wastewater treatment system. The method comprises: providing a bio-electrochemical sensor; measuring an electrical output of the bio-electrochemical sensor and correlating the output with a metabolic activity of exo-electrogenic bacteria present in the system; delivering one or more organic carbon compounds into the system; monitoring a change in the electrical output in response to the one or more organic carbon compounds, the electrical output corresponding to a value representing the amount of the one or more organic carbon compounds in the wastewater treatment system; and adjusting the delivery of the one or more organic carbon compounds in response to a change in the electrical output.

The one or more organic carbon compounds may comprise a volatile fatty acid, an organic acid, or a complex organic compound. The one or more organic carbon compounds may comprise a volatile fatty acid. The volatile fatty acid may be acetic acid, propionic acid, butyric acids, or a combination thereof.

The change in electrical output may be monitored over a period of time.

The adjusting step may comprise real time adjustments in the delivery of the one or more organic carbon compounds throughout the phosphorous removal process in response to changes in the electrical output. The delivery of the one or more organic carbon compounds may be adjusted in response to a change in electrical output beyond a threshold. The threshold may be a deviation of greater than about 10% from an operating electrical output. The threshold may represent a change in a ratio of the value representing the amount of one or more organic carbon compounds to a value representing the amount of phosphorous in the system. The delivery of the one or more organic carbon compounds may initiate, adjust, maintain, or stop carbon addition of the phosphorous removal process. The ratio may be less than about 10:1; less than about 15:1; less than about 20:1; less than about 25:1; less than about 30:1; less than about 35:1; less than about 40:1; less than about 45:1; or less than about 50:1.

In another aspect, the present disclosure provides a bio-electrochemical sensor for monitoring metabolic activity of a population of exo-electrogenic bacteria in response to one or more organic carbon compounds in a wastewater treatment system. The sensor comprises: an electrode pair comprising an anode and a cathode, the anode in electrical communication with the exo-electrogenic bacteria for receiving electrons therefrom; a current sensor for measuring electron flow between the anode and the cathode and producing an electrical output that correlates with metabolic activity of the exo-electrogenic bacteria and corresponds to a value representing the amount of the one or more organic carbon compounds in the wastewater treatment system; and a power source in electrical communication with the electrode pair for delivering a voltage across the electrode pair.

The current sensor may comprise a terminal electron acceptor in electrical communication with the cathode for receiving electrons therefrom, and a resistor in electrical communication with the terminal electron acceptor, wherein electric current is measured across the resistor.

In another aspect, the present disclosure provides a bio-electrochemical sensor for monitoring metabolic activity of a population of exo-electrogenic bacteria in response to one or more organic carbon compounds in a wastewater treatment system. The sensor comprises: a support comprising a bio support material for supporting the growth of exo-electrogenic bacteria; at least one electrode pair connected to the support, the at least one electrode pair comprising an anode and a cathode, where the exo-electrogenic bacteria are in proximity to the anode and release electrons to the anode, the released electrons flowing from the anode to the cathode; a power source in electrical communication with the electrode pair for delivering a voltage across the electrode pair; a terminal electron acceptor electrically coupled to the cathode for receiving electrons from the cathode and for generating an electrical output that correlates with metabolic activity of the exo-electrogenic bacteria and corresponds to a value representing the amount of the one or more organic carbon compounds in the wastewater treatment system; and a resistor electrically coupled to the terminal electron acceptor, wherein the output is measured across the resistor, using a data acquisition system.

The terminal electron accepter may be a non-oxygen electron acceptor. The non-oxygen electron acceptor may be H+ or $CO_2$.

The exo-electrogenic bacteria may comprise one or more of *Geobacter sulfurreducens, Geobacter metaloreducens, Pseudomonas aeruginosa,* and *Shewanella putrefaciens*. The exo-electrogenic bacteria may comprise *Geobacter sulfurreducens*.

The electrical output may be monitored to determine a value representing the amount of the one or more organic carbon compounds in the system at a steady-state. The electrical output may be monitored to determine a value representing the amount of the one or more organic carbon compounds in the system at a steady-state so that delivery of one or more organic carbon compounds can be initiated. The electrical output may be monitored as one or more organic carbon compounds are delivered into the system so that delivery adjustments can be made in real-time.

The wastewater treatment system may be an anaerobic or anoxic digestion system, and the bio-electrochemical sensor may be located within the anaerobic or anoxic digestion system. The anoxic or anaerobic digestion system may be a denitrifying tank. The anoxic or anaerobic digestion system may be an anaerobic phosphorous removal tank. The anoxic or anaerobic digestion system may comprise nitrate at a concentration from about 5 mg/L to about 100 mg/L, bio-available carbon at a concentration from 0 mg/L to about 100 mg/L, oxygen at a concentration of about ≤2 mg/L, or a combination thereof.

The one or more organic carbon compounds may comprise a volatile fatty acid, an organic acid, or a complex organic compound. The one or more organic carbon compounds may comprise a volatile fatty acid. The volatile fatty acid may be acetic acid, propionic acid, butyric acids, or a combination thereof.

In another aspect, the present disclosure provides a use of the sensor as herein described for monitoring metabolic activity of exo-electrogenic bacteria during a nitrogen removal process to adjust delivery of one or more organic carbon compounds to initiate, adjust, maintain, or stop nitrification of the nitrogen removal process.

In another aspect, the present disclosure provides a use of the sensor as herein described for monitoring metabolic activity of exo-electrogenic bacteria during a nitrogen removal process to adjust delivery of one or more organic carbon compounds to initiate, adjust, maintain, or stop simultaneous nitrification and denitrification of a nitrogen removal process.

In another aspect, the present disclosure provide a use of the sensor as herein described for monitoring metabolic activity of exo-electrogenic bacteria during a nitrogen removal process to adjust delivery of one or more organic carbon compounds to initiate, adjust, maintain, or stop denitrification of a nitrogen removal process.

In another aspect, the present disclosure provides a use of the sensor as herein described for monitoring metabolic activity of exo-electrogenic bacteria during a phosphorous removal process to adjust delivery of one or more organic carbon compounds to initiate, adjust, maintain, or stop carbon addition of a phosphorous removal process.

In another aspect, the present disclosure provides a system as herein described, wherein the sensor is the sensor as herein described.

In another aspect, the present disclosure provides a method as herein described, wherein the bio-electrochemical sensor is the sensor as herein described.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of examples only, with reference to the attached Figures.

DETAILED DESCRIPTION

Figure 1:
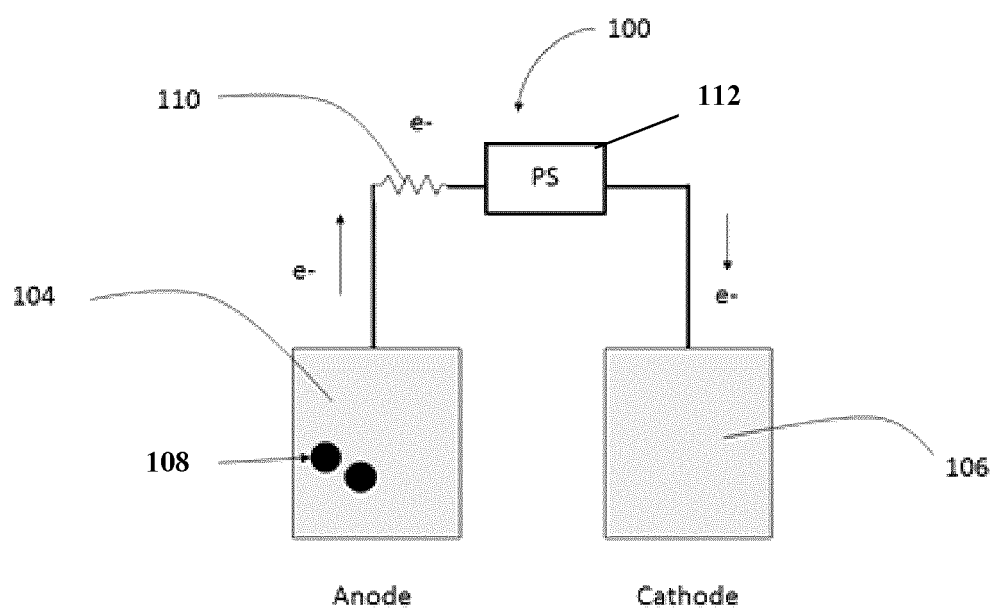
FIG. 1 is an illustration of an exemplary bio-electrochemical sensor according to the present disclosure.

Generally, the present disclosure provides a system for monitoring one or more organic carbon compounds in a wastewater treatment system. The system comprises a bio-electrochemical sensor to monitor metabolic activity of a population of exo-electrogenic bacteria and provide an electrical output corresponding with the metabolic activity. The bio-electrochemical sensor comprises an electrode pair and a power source to deliver a voltage across the electrode pair. The system further comprises an electrical output analyzer to analyze the electrical output and correlate the electrical output with a value representing the amount of the one or more organic carbon compounds in the wastewater treatment system.

The present disclosure also provides a system for controlling the delivery of one or more organic carbon compounds to a wastewater treatment system. The system comprises a bio-electrochemical sensor to monitor metabolic activity of a population of exo-electrogenic bacteria and provide an electrical output correlating with the metabolic activity. The bio-electrochemical sensor comprises an electrode pair and a power source to deliver a voltage across the electrode pair. The system further comprises an electrical output analyzer to analyze the electrical output and correlate the electrical output with a value representing the amount of the one or more organic carbon compounds in the wastewater treatment system, and provide a signal to a controller, and a pump operably coupled to the controller to control the delivery of the one or more organic carbon compounds in response to the signal.

The present disclosure further provides a method of monitoring one or more organic carbon compounds in a wastewater treatment system. The method comprises the step of: applying power to a bio-electrochemical sensor; measuring an electrical output of the bio-electrochemical sensor and correlating the output with metabolic activity of exo-electrogenic bacteria present in the system; and correlating the electrical output with the one or more organic carbon compounds in the wastewater treatment system.

The present disclosure further provides a method of controlling the delivery of one or more organic carbon compounds in a wastewater treatment system. The method comprises the steps of: applying power to a bio-electrochemical sensor; measuring an electrical output of the bio-electrochemical sensor and correlating the output with metabolic activity of exo-electrogenic bacteria present in the system; delivering the one or more organic carbon compounds into the system; monitoring a change in the electrical output in response to the one or more organic carbon compounds; and adjusting the delivery of the one or more organic carbon compounds in response to a change in the electrical output.

The present disclosure further provides a method of controlling a nitrogen removal process in a wastewater treatment system. The method comprises the steps of: applying power to a bio-electrochemical sensor; measuring an electrical output of the bio-electrochemical sensor and correlating the output with a metabolic activity of exo-electrogenic bacteria present in the system; delivering one or more organic carbon compounds into the system; monitoring a change in the electrical output in response to the one or more organic carbon compounds, the electrical output corresponding to a value representing the amount of the one or more organic carbon compounds in the wastewater treatment system; and adjusting the delivery of the one or more organic carbon compounds in response to a change in the electrical output.

The present disclosure further provides a method of controlling a phosphorous removal process in a wastewater treatment system. The method comprises the steps of: providing a bio-electrochemical sensor; measuring an electrical output of the bio-electrochemical sensor and correlating the output with a metabolic activity of exo-electrogenic bacteria present in the system; delivering one or more organic carbon compounds into the system; monitoring a change in the electrical output in response to the one or more organic carbon compounds, the electrical output corresponding to a value representing the amount of the one or more organic carbon compounds in the wastewater treatment system; and adjusting the delivery of the one or more organic carbon compounds in response to a change in the electrical output.

The present disclosure further provides a bio-electrochemical sensor for monitoring metabolic activity of a population of exo-electrogenic bacteria in response to one or more organic carbon compounds in a wastewater treatment system. The sensor comprises: an electrode pair comprising an anode and a cathode, the anode in electrical communication with the exo-electrogenic bacteria for receiving electrons therefrom; a current sensor for measuring electron flow between the anode and the cathode and producing an electrical output that correlates with metabolic activity of the exo-electrogenic bacteria and corresponds to a value representing the amount of the one or more organic carbon compounds in the wastewater treatment system; and a power source in electrical communication with the electrode pair for delivering a voltage across the electrode pair.

The present disclosure further provides a bio-electrochemical sensor for monitoring metabolic activity of a population of exo-electrogenic bacteria in response to one or more organic carbon compounds in a wastewater treatment system. The sensor comprises: a support comprising a bio support material for supporting the growth of exo-electrogenic bacteria; at least one electrode pair connected to the support, the at least one electrode pair comprising an anode and a cathode, where the exo-electrogenic bacteria are in proximity to the anode and release electrons to the anode, the released electrons flowing from the anode to the cathode; a power source in electrical communication with the electrode pair for delivering a voltage across the electrode pair; a terminal electron acceptor electrically coupled to the cathode for receiving electrons from the cathode and for generating an electrical output that correlates with metabolic activity of the exo-electrogenic bacteria and corresponds to a value representing the amount of the one or more organic carbon compounds in the wastewater treatment system; and a resistor electrically coupled to the terminal electron acceptor, wherein the output is measured across the resistor, using a data acquisition system.

The present disclosure also provides uses of the sensors according to the present disclosure for monitoring metabolic activity of exo-electrogenic bacteria during a nitrogen removal process or a phosphorous removal process.

Without being bound by theory, the exo-electrogenic bacteria as presently disclosed function by oxidizing wastewater components, for example, bio-available carbon, and preferentially transfers electrons extracellularly to an electrode surface. The rate at which electrons are transferred to the electrode correlates with the metabolic activity of the exo-electrogenic bacteria or biofilm. The exo-electrogenic bacteria generally reflect the population of microbes suspended in the wastewater treatment system. The data produced directly from the systems, methods, and sensors described herein may thus be used to monitor the metabolic activity of the microbes to indicate events affecting the resident microbiology in the wastewater treatment system, for example, the introduction, presence, adjustment, or depletion of one or more organic carbon compounds in the system. Real-time communication between wastewater treatment bacteria or biofilms and operational control of the wastewater treatment system may allow a user to control, adjust and/or optimize wastewater treatment system performance in real-time, and enhance system performance.

A wastewater treatment system includes any wastewater treatment system that converts wastewater into an effluent that can either be discharged, returned to a water cycle, or reused. In some examples according to the present disclosure, the wastewater treatment process involves anaerobic digestion, for example, an anaerobic or anoxic suspended growth digestion system, in which microbes break down biodegradable material or contaminants in the absence of or low concentrations of oxygen, for example, below about 2 mg/L of oxygen in solution. In some examples according to the present disclosure, the wastewater treatment systems involve a nitrogen removal process or a phosphorous removal process, which are both microbially facilitated and comprise aerobic and anaerobic components. The nitrogen removal process comprises one or more tanks comprising a nitrification or nitrifying tank, which comprises an aerobic environment, and a denitrification or denitrifying tank, which comprises an anaerobic or anoxic environment. The phosphorous removal process comprises one or more tanks comprising an anaerobic environment for POA feeding, and an aerobic environment for POA phosphorous uptake.

The presently disclosed systems, methods, and sensors may provide a stable and consistent electrical output (e.g., microbe-electrode electron transfer): (1) in the presence of competing electron sinks, such as nitrate and oxygen, during a nitrogen removal process or a phosphorous removal process; (2) during a nitrogen removal process or a phosphorous removal process where bio-available carbon is limited; or (3) a combination thereof. Competing electron sinks would otherwise be considered inhibitory to anodic electron transfer, and thus inhibitory to systems, methods, and bio-electrochemical sensors as described herein. Low or limited bio-available carbon that would otherwise be considered to be undetectable or detectable at insufficient resolution may be detected with sufficient resolution using systems, methods, or sensors according to the present disclosure. The herein disclosed systems, methods, and sensors may provide a stable and consistent electrical output in the presence of a relatively high concentration of nitrate, and/or trace amounts of oxygen. As used herein, stable refers to a signal that displays either a recurring pattern (e.g. hourly, daily, weekly, monthly), or a signal where the output does not dramatically shift in an unpredictable manner overtime (e.g., has a stable output). As used herein, a stable output is one where the steady state or recurring output pattern does not change by more than about 10% over a set period of time, for example, 24 hours.

A relatively high concentration of nitrate may be from about 5 mg/L to about 100 mg/L of nitrate in solution, for example, about 5 mg/L; about 10 mg/L; about 15 mg/L; about 20 mg/L; about 25 mg/L; about 30 mg/L; about 40 mg/L; about 50 mg/L; about 60 mg/L; about 70 mg/L; about 80 mg/L; about 90 mg/L; about 100 mg/L; or the concentration is from any one of the concentrations listed above to any other of the concentrations listed above. In preferred examples according to the present disclosure, a relatively high concentration of nitrate is from about 5 mg/L to about 30 mg/L of nitrate in solution. Trace amounts of oxygen may be less than about 2 mg/L of oxygen in solution, for example, less than about 2.0 mg/L; less than about 1.5 mg/L; less than about 1.0 mg/L; less than about 0.5 mg/L; 0 mg/L; or the concentration is from any one of the concentrations listed above to any other of the concentrations listed above. The herein disclosed systems, methods, and sensors may provide a stable and consistent electrical output where bio-available carbon is low or limited. A low or limited bio-availability of carbon may be from 0 mg/L to about 100 mg/L of bio-available carbon in solution, for examples, 0 mg/L; about 5 mg/L; about 10 mg/L; about 15 mg/L; about 20 mg/L; about 25 mg/L; about 30 mg/L; about 40 mg/L; about 50 mg/L; about 60 mg/L; about 70 mg/L; about 80 mg/L; about 90 mg/L; about 100 mg/L; or the concentration is from any one of the concentrations listed above to any other of the concentrations listed above. In preferred examples according to the present disclosure, a relatively low concentration of bio-available carbon is from 0 mg/L to about 30 mg/L of bio-available carbon in solution.

In the context of the present disclosure, bio-available carbon is any organic carbon compound that metabolically activates exo-electrogenic bacteria, for example, a volatile fatty acid, methanol, ethanol, acetate, acetic acid, glycerol, molasses sugar water, MicroC™, or a combination thereof. In the context of the present disclosure, biochemical oxygen demand (BOD) and chemical oxygen demand (COD) represent types of measurements used to determine the amount of organic carbon compounds present in a wastewater treatment system. The amount of organic carbon compound present in the wastewater treatment system forms a major subset of BOD, and in turn, BOD forms a major subset of COD.

Exo-electrogenic bacteria may be any bacteria that has the ability to transfer electrons extracellularly, and that is metabolically activatable by at least one component in the wastewater treatment system. Metabolically activated refers to the anoxic or anaerobic digestion of wastewater components, such as volatile fatty acids, organic acids, and complex organic compounds resulting in the production of electrons. As used herein, complex organic compounds refer to organic compounds that are required to be broken down to short chain fatty acids (or volatile fatty acids) that can be used for key nutrient cycling in biological systems. Examples of complex organic compounds are cellulose and sucrose. In some examples according to the present disclosure, the exo-electrogenic bacteria may include one of more of *Geobacter sulfurreducens*, *Geobacter metaloreducens*, *Pseudomonas aeruginosa*, and *Shewanella putrefaciens*. The number and type of exo-electrogenic bacteria may depend on the type of wastewater system. In some preferred examples, the exo-electrogenic bacteria include *Geobacter sulfurreducens*.

In the context of the present disclosure, it should be understood that reference to "microbe", "microorganism" or "bacteria" includes one or more bacterium. Typically, a wastewater treatment system will comprise more than one type of resident bacteria. The terms "microbe and "microorganism" are used interchangeably herein to describe the one or more resident bacterium in the wastewater treatment system. The terms "electrogenic" and "exo-electrogenic" bacteria are used interchangeably herein.

Herein described systems and methods can produce a substantially constant electrical output or current under constant wastewater treatment system conditions. This may, for example, be referred to as a steady-state current. The steady-state current may be correlated with a value representing the amount of one or more organic carbon compounds, for example, volatile fatty acids, in the wastewater treatment system. When, for example, an organic carbon compound is introduced, removed, or consumed in the system, or the wastewater treatment system is imbalanced, the metabolic activity of the microbial population can be impacted, resulting in a deviation from the steady-state current. Without being bound by theory, the presence of organic carbon compounds, for example volatile fatty acids, may cause an increase in exo-electrogenic metabolic activity due to, for example, additional electron transfer pathways and increased oxidation or reduction potential, which in turn may increase the current. This interaction between certain organic carbon compounds and bio-electrochemical sensor activity may be distinct and may allow a correlation between a change in current to the specific organic carbon compound. The correlation may be used to distinguish each organic carbon compound from a combination of compounds in the system.

Herein described systems and methods may initiate, increase, decrease, or discontinue the delivery of one or more organic carbon compounds in the wastewater treatment system in response to a signal produced as a result of a change in electric output when the electric output meets or exceeds a threshold. Herein described systems may comprise an electrical output analyzer, which refers to any processor in communication with the sensor and able to analyze the electrical output from the sensor and provide a signal, when appropriate, to cause an adjustment in the wastewater treatment system. In some examples according to the present disclosure, a signal is provided when the electrical output meets a threshold output or deviates from a reference output.

A threshold output is an output (such as a current measurement) at which the wastewater treatment system parameters are no longer at levels acceptable for the continuing operation or function of the wastewater treatment system. As would be known by one of skill in the art, determining what is considered an acceptable parameter level(s) for the operation or function of a wastewater treatment system will be dependent on, or determined by the specific wastewater treatment system. The threshold current or other output may represent a deviation from a reference operating electrical output of, for example, about 5%, about 10%, about 20%, about 50%, about 100% deviation, or the percentage is from any one of the percentages listed above to any other of the percentages listed above. The reference operating output may, for example, be a baseline or steady-state current. A skilled person, such as a manufacturer or an operator, will be able to determine acceptable levels of deviation. The threshold current may be pre-determined, for example, from previous methods; known values in the art; or a value determined using alternative methods known to a skilled person. In some examples according to the present disclosure, the threshold is determined relative to the current generated from the metabolic activity of the exo-electrogenic bacteria under standard operating conditions, for example, standard temperature, pH, pressure, and wastewater flow rate.

The deviation may be measured over time; and, a threshold may be set based on one or both of the deviation and time. For example, a deviation may be measured over a period of from about 1 second to about 24 hours, for example, about 1 second, 2 seconds, 3 seconds, 5 seconds, 10 seconds, 20 seconds, 30 seconds, 60 seconds, 120 seconds, 240 seconds, 500 seconds, 1000 seconds, 3600 seconds, 5000 seconds, 10,000 seconds, 18,000 seconds; or about 1 second to about 12 hours; or the time is from any one of the times listed above to any other of the times listed above. In some examples according to the present disclosure, measurement is initiated about 1 second after the addition of an organic carbon compound, and the wastewater treatment system is monitored for a deviation for about 12 hours thereafter. In some examples according to the present disclosure, measurement is initiated about 10 seconds after the addition of an organic carbon compound, and the wastewater treatment system is monitored for a deviation for about 1 hour thereafter. In some examples according to the present disclosure, a threshold deviation may be a deviation of greater than about 10% from the reference operating electrical output over about 2 hours or over about 3 hours from the introduction of one or more organic carbon compounds into the wastewater treatment system. In some examples according to the present disclosure, a deviation may be measured in less than about 15 seconds; less than about 10 seconds; less than about 5 seconds; less than about 2 seconds; less than about 1 second, or the time is from any one of the times listed above to any other of the times listed above, after the introduction of one or more organic carbon compounds.

The impact of the organic carbon compound may be visualized by the operator or signaled by a system if it has an impact on the bio-electrochemical sensor. This variation or deviation in output from the bio-electrochemical sensor may be used to initiate, discontinue, adjust, maintain, or control the addition of the organic carbon compound. The amount of time after the introduction of one or more organic carbon compounds in which a change in current can be measured will depend on various factors, for example, components in the wastewater treatment system, volumetric size of the wastewater treatment system, the type and amount of exo-electrogenic bacteria, or a combination thereof.

The herein described systems and methods may be used to adjust the amount, type, or combination thereof of organic carbon compounds delivered into the wastewater treatment system. In some examples according to the present disclosure, once it is determined that the measured current has reached the determined threshold, a signal is sent to a pump that controls the delivery of the organic carbon compound into the wastewater treatment system, which in turn decreases or discontinues the delivery of the organic carbon compound. Once it is determined that the measured current is within an acceptable range or within the threshold output, a further signal may be sent to the pump to initiate or increase the delivery of the organic carbon compound. In other examples according to the present disclosure, a signal is sent to the pump to initiate or increase the delivery of the organic carbon compound. Once it is determined that the measured current is within an acceptable range or within the threshold output, a further signal may be sent to the pump to decrease or discontinue the delivery of the organic carbon compound.

In some examples according to the present disclosure, an operator affects an adjustment on the wastewater treatment system in response to signals provided by the methods, systems, and bio-electrochemical sensors described herein. In other examples according to the present disclosure, a processor running an algorithm and in communication with the presently disclosed systems and bio-electrochemical sensors predicts imbalances on the wastewater treatment system based on the electrical output provided by the herein described systems, methods, and bio-electrochemical sensors, and adjusts the wastewater treatment system in response to the prediction. In some examples according to the present disclosure, the processor is a predictive learning machine.

In some examples according to the present disclosure, when the change in electrical output of the herein described sensors meets a threshold, one or more organic carbon compounds are delivered to the system to initiate a nitrogen removal process (nitrification and denitrification). Delivery of the one or more organic carbon compounds will depend on the type of nitrogen removal process as well as the wastewater plant treatment system or plant parameters. Examples of nitrogen removal processes are chemical addition, step feed, or shifting tank dynamics. During the nitrogen removal process, the change in electrical output may meet a second threshold and the delivery of one or more organic carbon compounds is stopped. In some examples, the delivery is stopped to end the nitrogen removal process, while in other examples, the delivery is stopped to adjust the amount of the one or more organic carbon compounds in the system to increase the efficiency of the nitrogen removal process. In some examples according to the present disclosure, during the nitrogen removal process, the change in electrical output may meet a threshold and the delivery of one or more organic carbon compounds is maintained at or near the threshold to maintain the efficiency of the nitrogen removal process.

The electrical output of herein described systems, methods and sensors may correlate to a value representing the amount of one or more organic carbon compounds in a nitrogen removal process. In some examples, this value will be sufficiently low for initiating nitrification of a nitrogen removal process. Nitrification can take up to 5 weeks to produce enough nitrifying bacteria to commence treating ammonia. Therefore, monitoring the tank, recycle, and/or sludge where nitrification is desired, to confirm the organic carbon compound concentrations are sufficiently low enough to initiate nitrification, may increase the efficiency of the nitrification process as well as the cost-efficiency.

The electrical output of herein described systems, methods and sensors may be used to predict a favorable time to initiate nitrification, denitrification, or simultaneous nitrification and denitrification of a nitrogen removal process by: (1) determining the BOD concentration in the system; (2) determining a ratio of a value representing the amount of one or more organic carbon compounds in the system to a value representing the amount of nitrogen in the system; or (3) a combination thereof. This BOD concentration and/or ratio may be monitored over time to enhance the nitrification and/or denitrification process. Most conventional wastewater treatment systems or plants sample manually and have daily or weekly tests from which the concentration of nitrogen in the wastewater treatment system is measured. Monitoring the changes in the BOD concentration and/or ratio of the amount of organic carbon compound, for example VFA, in the wastewater treatment system to the amount of nitrogen in the wastewater treatment system over time, may be extrapolated to predict a favorable time to initiate a nitrification, simultaneous nitrification and denitrification, and/or denitrification process. In some examples according to the present disclosure, the BOD concentration for initiating a nitrification process or a simultaneous nitrification and denitrification process is from 0 mg/L to less than about 30 mg/L BOD, for example, less than about 0 mg/L; less than about 1 mg/L; less than about 2 mg/L; less than about 5 mg/L; less than about 10 mg/L; less than about 15 mg/L; less than about 20 mg/L; less than about 25 mg/L; less than about 30 mg/L; or the concentration is between any one of the concentrations listed above to any other of the concentrations listed above. In some examples according to the present disclosure, a ratio of BOD:nitrogen or acetate:nitrogen (mass:mass) for initiating a nitrification process or a simultaneous nitrification and denitrification process is from about 0:1 to about 10:1, for example, about 0:1; about 1:1, about 2:1; about 3:1; about 4:1; about 5:1; about 6:1; about 7:1; about 8:1; about 9:1; about 10:1; or the ratio is between any one of the ratios listed above to any other of the ratios listed above. In some examples according to the present disclosure, the ratio of BOD:nitrogen (mass:mass) for initiating a denitrification process is from greater than about 4:1 to greater than about 12:1, for example, greater than about 4:1; greater than about 5:1; greater than about 6:1; greater than about 7:1; greater than about 8:1; greater than about 9:1; greater than about 10:1; greater than about 11:1; greater than about 12:1; or the ratio is between any one of the ratios listed above to any other of the ratios listed above. A skilled person would understand that the BOD concentration and/or ratio can be affected by the type of organic carbon compound in the wastewater treatment system, the species of microbes present in the wastewater treatment system, solids retention time and sludge yields of the microbial populations, or a combination thereof.

For a nitrogen removal process, the herein described systems, methods, or sensors may be used to predict that the concentration of VFA in a nitrification chamber is sufficiently low to allow for this reaction to take place. In some examples, about 10 mg/L or less of VFA is present in the solution for nitrification to take place. In some examples, about 10 mg/L of VFA is present in the solution for nitrification to take place. In other examples, about 8 mg/L or less, or about 6 mg/L or less, or about 4 mg/L or less, or about 2 mg/L or less, or 0 mg/L, or any value there between of VFA is present in the solution for nitrification to take place, or the concentration of VFA is from any one of the concentrations listed above to any other of the concentrations listed above. For denitrification to take place, herein described systems, methods, or sensors may be used to predict the concentration of available VFA in solution and control the addition of additional VFA (or the rate of VFA/carbon addition) to a denitrification chamber. In some examples of simultaneous nitrification and denitrification processes, the electrical output of herein described systems, methods and sensors may be used to determine an amount of organic carbon compound in the wastewater treatment system to optimize both the nitrogen removal process (i.e., nitrification and denitrification). Too much organic carbon compound in the wastewater treatment system may inhibit the nitrification process whereas too little organic carbon compound in the wastewater treatment system may inhibit the denitrification process. This electrical output may be monitored over time to optimize the both processes.

In some examples according to the present disclosure, when the electrical output of herein described systems, methods and sensors meets a threshold, one or more organic carbon compounds may be delivered to the wastewater treatment system to initiate a carbon addition process as part of a phosphorous removal process. Delivery of the one or more organic carbon compounds will depend on the type of phosphorous removal process, as well as the wastewater treatment system or plant parameters. One example of a phosphorous removal process is the Enhanced Biological Phosphorous Removal. During carbon addition, the change in electrical output of herein described systems, methods and sensors may meet a second threshold and the delivery of one or more organic carbon compounds is stopped. In some examples, the delivery is stopped to end the carbon addition process and initiate a phosphorous accumulation process, while in other examples, the delivery is stopped to adjust the amount of the one or more organic carbon compounds in the wastewater treatment system to increase the efficiency of the carbon addition process. In some examples, during carbon addition, the change in electrical output of herein described systems, methods and sensors may meet a threshold and the delivery of one or more organic carbon compounds may be maintained at or near the threshold to maintain the efficiency of the carbon addition process.

The electrical output of herein described systems, methods and sensors may correlate to a value representing the amount of one or more organic carbon compounds in a phosphorous removal process. In some examples according to the present disclosure, this value will be sufficiently low for initiating carbon addition of a phosphorous removal process. In some examples, the electrical output of herein described systems, methods and sensors may be used to predict a favorable time to initiative carbon addition by determining a ratio of a value representing the amount of one or more organic carbon compounds in the wastewater treatment system to a value representing the amount of phosphorous in the system. Most conventional wastewater treatment systems or plants sample manually and have daily or weekly tests from which the concentration of phosphorous in the wastewater treatment system is measured. Monitoring the changes in the ratio of the amount of organic carbon compound, for example VFA, in the wastewater treatment system to the amount of phosphorus in the wastewater treatment system over time, may be extrapolated to predict a favorable time to initiate carbon addition. The ratio may also be monitored over time to enhance the carbon addition process. In some examples according to the present disclosure, the ratio of BOD:phosphorous (mass:mass) for initiating carbon addition is from less than about 10:1 to less than about 50:1, for example, less than about 10:1; less than about 15:1; less than about 20:1; less than about 25:1; less than about 30:1; less than about 35:1; less than about 40:1; less than about 45:1; less than about 50:1; or the ratio is between any one of the ratios listed above to any other of the ratios listed above. During the carbon addition process, the ratio may meet a threshold and the delivery of one or more organic carbon compounds is started and a phosphorous accumulation process is initiated. A skilled person would understand that this ratio can be affected by the type of organic carbon compound in the system, the species of microbes present in the system, solids retention time and sludge yields of the microbial populations, or a combination thereof.

The electrical output of herein described systems, methods and sensors may be used to select for PAO organisms suitable for phosphorous accumulation. The PAO organism may be Tetrasphaera. In some examples according to the present disclosure, the herein described systems and sensors may carry out synergistic relationships with Tetrasphaera and therefore, the systems and sensors may act as a surrogate for the health of the Tetrasphaera biology. When a system or sensor is not measuring a sufficient amount of VFAs for Tetrasphaera to function, the electrical output may deviate indicating that action should be taken. This use may help avoid PAO processes from getting upset, which can save the operations staff considerable issues. If a phosphorous removal process is being performed in a SBR or oxidation ditch, the herein described systems and sensors may be used to guide the retention times of each compartment or loading to the entire system. Since both of these treatment processes can control the retention time and order of the zones, the systems and sensors can be used to optimize this process. This may result in more efficient operation as well as reduced costs. The herein described systems and sensors may be installed in a collection system used for the creation of the required VFA concentrations for a wastewater treatment system or plant.

Optionally, herein described methods and systems may comprise a controller, which receives a signal from the electrical output analyzer and, in turn, controls the delivery of one or more organic carbon compounds into the wastewater treatment system via a pump. In the context of the present disclosure, the controller is any processor in communication with the bio-electrochemical sensor that accepts a signal from the electrical output analyzer and relays the signal to a pump. In some examples according to the present disclosure, the presently disclosed bio-electrochemical sensors may be used in methods or systems for controlling a pump via an electrical output analyzer to deliver optimal concentrations of organic carbon compounds.

Optionally, herein described methods and systems may control a valve to control the amount of one or more organic carbon compounds in the wastewater treatment system. In some examples according to the present disclosure, the electrical output analyzer provides a signal to a controller, which in turn controls the delivery of the wastewater into the wastewater treatment system via a valve coupled to the wastewater treatment system. In the context of the present disclosure, the valve is any device that initiates, discontinues or controls the flow of material into the wastewater treatment system. The valve may direct or redirect the flow of: (2) one or more organic carbon compounds into the system; (2) wastewater out of the system; or (3) a combination thereof. In some examples according to the present disclosure, the presently disclosed bio-electrochemical sensors may be used in methods or systems for controlling a valve via an electrical output analyzer to control the delivery of wastewater into the wastewater treatment system.

The herein described methods and systems may monitor metabolic activity of a population of exo-electrogenic bacteria at any location within the wastewater treatment system. In some preferred examples, the herein described systems and sensors may be positioned in a zone of a bioreactor of a wastewater treatment system that: (1) has stable and consistent flow; (2) is not impacted or narrowly impacted by hydraulic dead zones; (3) is representative of the activity in the wastewater treatment system being diagnosed; or (4) a combination thereof.

The herein described systems and sensors may be placed within one or more vessels of a nitrogen removal process, within one or more vessels of a phosphorous removal process, or a combination thereof. Optionally, the herein described systems and sensors may be placed near the front of a nitrogen removal reactor vessel or a phosphorous removal reactor vessel, for example when determining the amount of one or more organic carbon compounds that are reaching and/or entering a nitrogen removal reactor vessel or a phosphorous removal reactor vessel is desirable. Optionally, the herein described systems and sensors may be placed at a location where any recycle stream, organic carbon compound addition stream, chemical addition stream, or a combination thereof enters a nitrogen removal reactor vessel or a phosphorous removal reactor vessel, for example when determining the amount of one or more organic carbon compounds entering the nitrogen removal reactor vessel or phosphorous removal reactor vessel is desirable. Optionally, the herein described systems and sensors may be placed at a location approximately half-way through a nitrogen removal reactor vessel or a phosphorous removal reactor vessel, for example, when determining the amount of one or more organic carbon compounds is persisting or being used for nutrient removal is desirable. Optionally, the herein described systems and sensors may be placed at a location near the back of a nitrogen removal reactor vessel or a phosphorous removal reactor vessel, for example when determining the amount of one or more organic compounds is exiting the nitrogen removal reactor vessel or phosphorous removal reactor vessel is desirable. Metabolic activity measured near the back of a nitrogen removal reactor vessel or a phosphorous removal reactor vessel may be useful for understanding whether there is excess carbon in the system, which may allow adjustments to increase the amount of nitrogen or phosphorous into the nitrogen removal reactor vessel or phosphorous removal reactor vessel. One or more locations of the herein described systems and sensors may allow a wastewater treatment system to adjust the amount of one or more organic carbon compounds provided into the wastewater treatment system to increase the efficiency of the system. Increasing efficiency of the wastewater treatment system may decrease operating costs by, for example, saving costs associated with transporting materials through the system, decease the costs for additional aeration energy to remove excess carbon, or a combination thereof. In some of the examples according to the present disclosure, the herein described systems and sensors are not placed in close proximity to a pump or mixer.

Optionally, the herein described systems and sensors may be placed near the front a wastewater treatment plant, for example, when understanding the amount of bio-available carbon entering into the system is desired. The front of the wastewater treatment plant may be an influent stream. The metabolic activity measured at the front of a wastewater treatment plant may be useful for: (1) adjusting the dosing of supplemental carbon; (2) adjusting the time of dosing of supplemental carbon; (3) adjusting dosing of side streams into the system to maintain the appropriate bio-available carbon for nitrogen and phosphorous removal processes; or (4) a combination thereof.

Optionally, the herein described systems and sensors may be placed in or following a solids handling or thickening tank, for example, a primary clarifier, for example, when understanding the amount of bio-available carbon that is settled in the primary clarifier is desirable. Generally, the more effective the upfront settling, the more carbon is removed. Accordingly, the metabolic activity measured in the primary clarifier may be useful to assist operators to make decisions of potentially removing or bypassing the primary clarifier to increase the carbon available for downstream processes or to adjust the amount of organic carbon compounds and nitrate in the clarifier, which can cause sludge to float as the nitrate is turned into nitrogen gas, which may compromise the ability of the clarifier to compact solids. Optionally, the herein described systems and sensors may be placed in a fermentation tank, for example when monitoring the fermentation levels is desired. Many water treatment facilities use either old primary clarifiers or other tanks to ferment wastewater to feed to the system. This fermented wastewater may be better suited for PAO organisms and nitrogen removing organisms. Optionally, the herein described systems and sensors may be placed in one or more side streams, for example when additional information on how steady the sides streams are and how and when to best incorporate them back into the wastewater treatment system or plant is desirable. Each solids separation step at a wastewater treatment plant (e.g. anaerobic digester supernatant, centrifuge filtrate, backwash from filters, pump and hauled wastewater, septage) may produce a highly concentrated waste stream with significant quantities of bioavailable carbon, nitrogen and phosphorous. In some examples, the side stream is returned to the front of the plant. In other examples, these side streams can be returned directly to a nutrient removal process to maintain a healthy bioavailable carbon to nutrient (nitrogen or phosphorous) ratio.

When wastewater treatment systems or plants are evaluating how to generate the required VFAs (fermentation products), the herein described systems and sensors may be used during their testing to quantify the performance of each unit of the wastewater treatment system. Wastewater treatment systems or plants typically look at using a collection system, one of the clarifiers on site, a thickener, a digester, an anaerobic process step or others. The herein described systems and sensors may be used to test different units to determine which would be the best for the wastewater treatment system. The herein describes systems and sensors may be used by designers to monitor the background concentrations of one or more organic carbon compounds throughout a phosphorous removal process to assist in the design of an appropriately sized EBPR systems.

Bio-electrochemical sensors according to the present disclosure are any sensors that can, with a voltage input, monitor the metabolic activity of microbes in a wastewater treatment system in real time, and provide an electrical output that correlates with their metabolic activity. For example, herein described sensors are bio-electrochemical sensors, which comprise an anode in electrical communication with an exo-electrogenic biofilm community. The anode of the one electrode pair may be in direct electrical communication with exo-electrogenic bacteria, for example, the exo-electrogenic bacteria may be attached to, grown on, or otherwise electrically coupled with, the anode. Alternatively, the sensor may be in indirect electrical communication with the exo-electrogenic bacteria, for example, but incorporating an electrical linker between the exo-electrogenic bacteria and the sensor. In the context of the present disclosure, the terms "electrical communication" or "electrically coupled" mean that electrons are transferable between the recited components. In some examples according to the present disclosure, components that are in "electrical communication" or are "electrically coupled" are connected by an electrical wire. In some examples according to the present disclosure, the exo-electrogenic bacteria are supported by a bio-support connected to the sensor. In the context of the present disclosure, a bio support material is any material that can support growth of exo-electrogenic bacteria. In some examples, the bio-support material is a metallic compound or alloy, a stainless steel compound or alloy, a carbon based compound or alloy, or a combination thereof. In some preferred examples, the bio-support is a corrosion resistant metallic compound or alloy, for example, stainless steel 316. In some examples according to the present disclosure, the exo-electrogenic bacteria are fixed directly to the bio support material. Alternatively, the exo-electrogenic bacteria are fixed to an intermediate component that is in electrical communication with the bio support material and the exo-electrogenic bacteria. In other examples, the exo-electrogenic bacteria are detachable from the bio support material. The exo-electrogenic bacteria may also be grown on the bio support material.

This anodic biofilm community oxidizes organic carbon compounds, for example volatile fatty acids, present in the wastewater treatment system, and donates electrons to the electrode surface. The rate at which electrons are transferred to the electrode correlates with the metabolic activity of the exo-electrogenic biofilm. The biofilm community associated with the anode generally reflects a value that represents the amount of one or more organic carbon compounds in the wastewater treatment system. The data produced directly from the bio-electrochemical sensor can thus be used to monitor events, for example toxic events, and system imbalances, affecting the resident microbiology in the wastewater treatment system. The herein described bio-electrochemical sensors can allow for real-time communication between wastewater treatment biofilms and the operational control of the wastewater treatment system. Correlations that are identified with available organic carbon compounds, Biochemical Oxygen Demand (BOD), or VFA can be used to better understand and enhance nitrogen and phosphorous removal events. This information can be used to control, adjust and/or enhance overall wastewater treatment system performance in real-time.

As illustrated in the examples, data generated from a bio-electrochemical sensor according to the present disclosure may provide a real-time and direct (linear correlation) to the concentration of volatile fatty acids (i.e. acetic acid). A real-time understanding of the VFA concentration may be used to enhance the nitrogen removal process.

Optionally, the bio-electrochemical sensors according to the present disclosure may comprise a power source in electrical communication with the electrode pair, for example when operating the bio-electrochemical sensor in an anaerobic environment is preferable. The power source may be any power-emitting instrument that applies a voltage across the electrode pair of the bio-electrochemical sensor. In some examples according to the present disclosure, the applied voltage is from 0.1 V to about 1.5 V, for example, about 0.1 V; 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V; or the voltage is between any one of the voltages listed above to any other of the voltages listed above. In some examples according to the present disclosure, the applied voltage is from about 0.3 V to about 0.9 V. Without being bound by theory, the applied voltage to the bio-electrochemical sensor may allow the sensor to utilize a non-oxygen terminal electron acceptor, for example, $H^+$ or $CO_2$. In the context of the present disclosure, a terminal electron acceptor refers to any component that receives or accepts an electron. In some examples, the terminal electron accepter is any conductive material that allows for an electrochemical reduction reaction, for example, the reduction of $H^+$ as a terminal electron acceptor in the production of hydrogen gas. As used herein, the phrase "oxygen terminal electron acceptors" refers to use of the compound dioxygen (i.e., $O_2$) as a terminal electron acceptor. In contrast, the phrase "non-oxygen terminal electron acceptors" refers to terminal electron acceptors that are not dioxygen (i.e., $O_2$); however, this is not meant to exclude terminal electron acceptors that may be comprised of oxygen atoms, such as but not limited to $CO_2$, etc.

Optionally, the bio-electrochemical sensors according to the present disclosure may comprise a current sensor. In the context of the present disclosure, a current sensor is any sensor that measures electron flow between the anode and the cathode, and produces an electrical output. In some examples, the current sensor comprises a terminal electron acceptor in electrical communication with the cathode for receiving electrons therefrom, and a resistor in electrical communication with the electrode pair, where electrical current is measured across the resistor. In the context of the present disclosure, a resistor refers to any electrical component that impedes electrical resistance. In some examples, the resistor operates in the range of from about 1 Ohm to about 10,000 Ohms, for example, 1 Ohm, 2 Ohms, 3 Ohms, 4 Ohms, 5 Ohms, 6 Ohms, 7 Ohms, 8 Ohms, 9 Ohms, 10 Ohms, 25 Ohms, 50 Ohms, 75 Ohms, 100 Ohms, 250 Ohms, 500 Ohms, 1,000 Ohms, 2,500 Ohms, 5,000 Ohms, 7,500 Ohms, 10,000 Ohms; or the electrical resistance is between any one of the electrical resistances listed above to any other of the electrical resistances listed above. In some examples, the resistor is a low-Ohm resistor (about 5 Ohms). Measuring an electrical output across the resistor refers to measuring the change in electrical potential before and after the resistor.

Optionally, bio-electrochemical sensors according to the present disclosure may be configured into a compact design, for example, by configuring the anode and cathode of the sensor in close proximity to one another. This compact design may allow the sensor to be immersed entirely into an anoxic or anaerobic environment, positioned within a reaction vessel in areas suitable for increasing accuracy of measurement, for better understanding the amount of one or more organic carbon compounds entering, being consumed, and/or exiting the reaction vessel, or a combination thereof. The compact design and ability to be immersed in the reaction vessel may also decrease the amount of equipment required to use the bio-electrochemical sensor in a wastewater treatment system; for example, by: (1) decreasing equipment that would otherwise be required to retrofit existing wastewater treatment systems to couple with an aerobic sensor; (2) decreasing equipment required to enable aerobic sensors to be in electrical communication with oxygen terminal electron acceptors; or (3) a combination thereof.

In the context of the present disclosure, "immersed" within or into an environment refers to wholly sinking the bio-electrochemical sensor within the environment. In some examples according to the present disclosure, a portion of the bio-electrochemical sensor is immersed into an anoxic or anaerobic wastewater treatment environment, for example, about 10%, about 25%, about 50%, about 75%, about 80%, about 85%, about 90%, about 95%, 100%, or the percentage is from any one of the percentages listed above to any other of the percentages listed above, of the surface area of a bio-electrochemical sensor is immersed into an anoxic or anaerobic wastewater treatment environment. In some examples according to the present disclosure, 100% of the surface area of the bio-electrochemical sensor is immersed into an anoxic or anaerobic wastewater treatment environment, for example when increasing the accuracy of monitoring one or more organic carbon compounds in a nitrogen or phosphorous removal process is desirable.

The compactness of the herein described bio-electrochemical sensors refers to the orientation and space between the anode and the cathode. Optionally, the anode and cathode are configured in parallel. In some examples according to the present disclosure, at least a portion of the anode overlaps with at least a portion of the cathode. The portion of overlap may refer to portions along the length of the electrodes. In some examples according to the present disclosure, the overlapping portion of the anode and the overlapping portion of the cathode are, independently, about 10%, about 20%, about 25%, about 50%, about 75%, 100%; or the percentage is from any one of the percentages listed above to any other of the percentages listed above, of the length of the electrode or cathode. In some examples according to the present disclosure, the distance between the overlapping portions of the anode and the cathode is about 1 mm, about 2 mm, about 3 mm, about 4 mm, about 5 mm, about 6 mm, about 7 mm, about 8 mm, about 9 mm, about 10 mm; or the distance is from any one of the distances listed above to any other of the distances listed above.

As noted above, the present disclosure provides a bio-electrochemical sensor for performing herein described methods, as well as for being incorporated into herein described systems. An exemplary sensor configuration is shown in FIG. 1. The sensor (100) generally comprises: an electrode pair comprising an anode (104) and a cathode (106), the anode (104) in electrical communication with the exo-electrogenic bacteria (108) for receiving electrons therefrom; a resistor (110) electrically coupled to the electrode pair, the electrical current being measured across the resistor (110); a power source (112) in electrical communication with the electrode pair for delivering voltage across the electrode pair; and a terminal electron acceptor (not shown) for receiving electrons from the cathode. Changes in electrical output may be used to optimize wastewater treatment system performance, for example, to determine optional delivery of one or more organic carbon compounds to the system. A change in electrical output may be measured against a set threshold to determine when an adjustment is needed.

Figure 2:
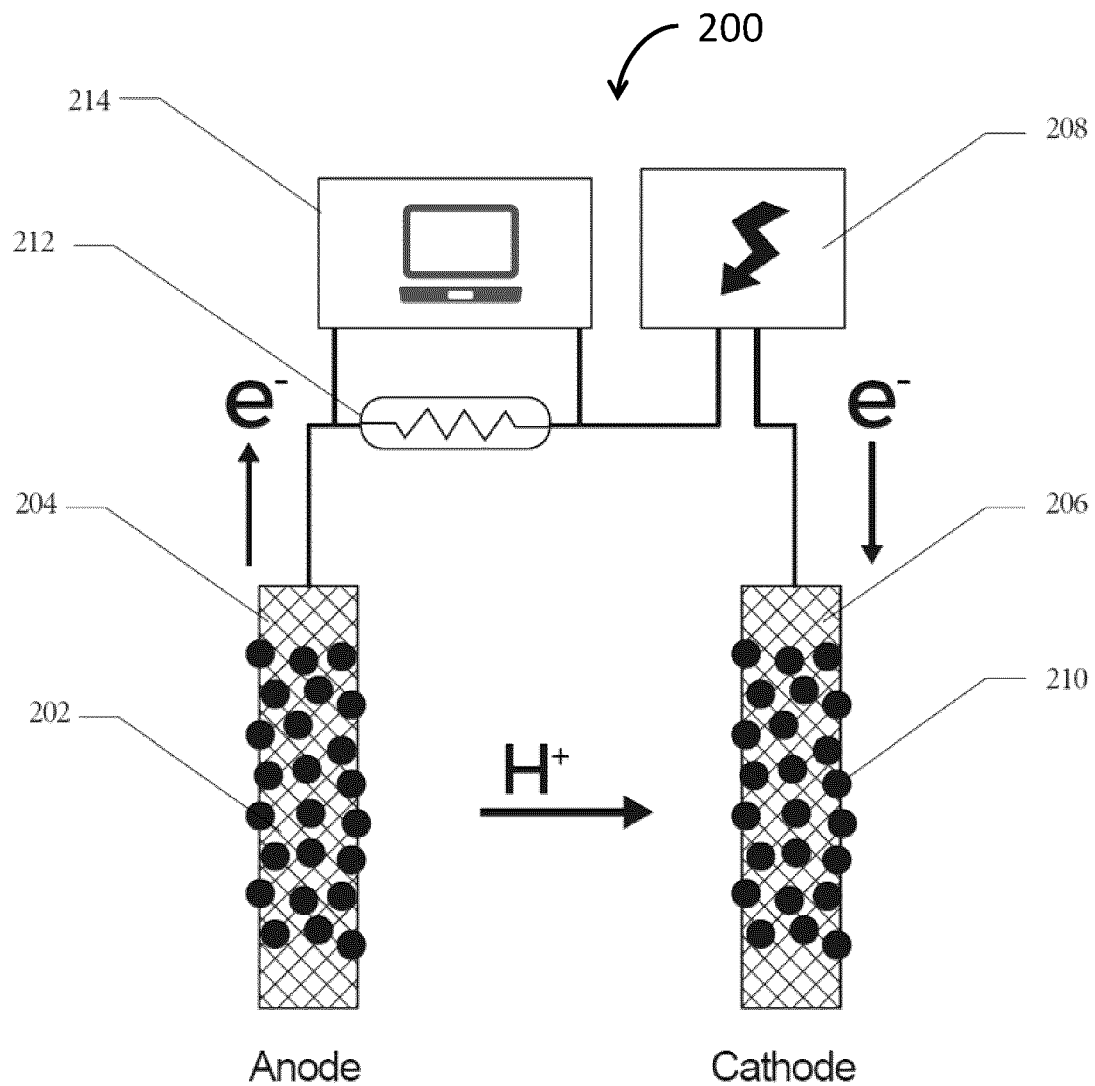
FIG. 2 is an illustration of another exemplary bio-electrochemical sensor according to the present disclosure.

Another exemplary bio-electrochemical sensor configuration is shown in FIG. 2. The sensor (200) comprises: a support comprising a bio support material for supporting growth of exo-electrogenic bacteria (202); an electrode pair connected to the support comprising a cathode (206) and an anode (204), the anode (204) in electrical communication with the exo-electrogenic bacteria (202) for receiving electrons therefrom; a power source (208) in electrical communication with the electrode pair (204, 206) for delivering a voltage across the electrode pair (204, 206); a terminal electron acceptor (210) electrically coupled to the cathode (206) for receiving electrons from the cathode (206) and for generating an electrical output that correlates with metabolic activity of the exo-electrogenic bacteria (202); and a resistor (212) electrically coupled to the terminal electron acceptor (210; H+), wherein the output is measured across the resistor using a data acquisition system or electrical output analyzer (214). Changes in electrical output may be used to optimize wastewater treatment system performance; for example, by monitoring the metabolic activity of a population of exo-electrogenic bacteria in response to one or more organic carbon compounds delivered to the wastewater treatment system, such that delivery of the organic carbon compounds can be adjusted, as needed in response to changes in the metabolic activity.

Figure 3A:
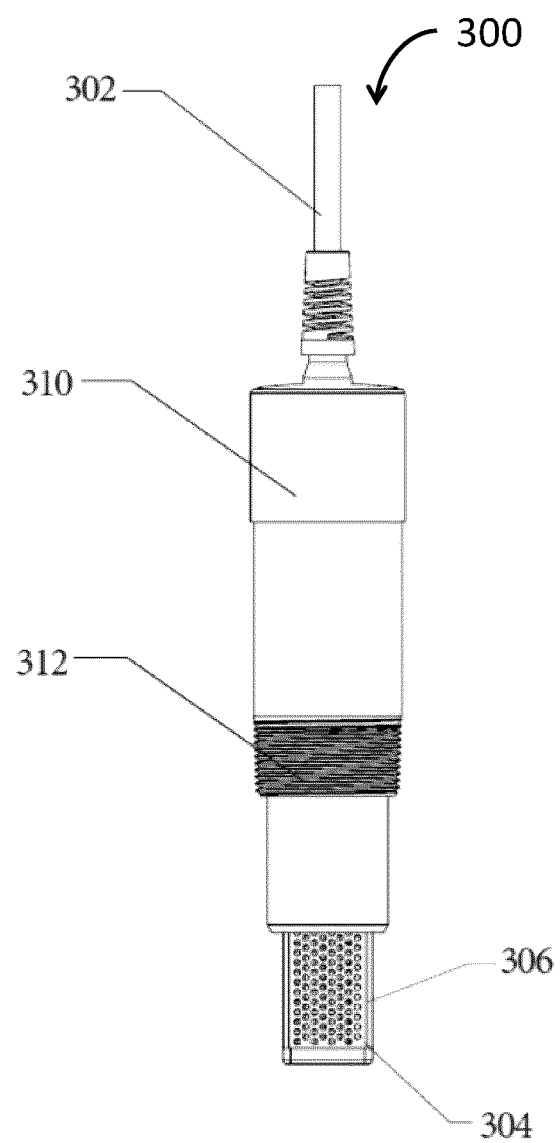
FIGS. 3A-3C are illustrations of an exemplary bio-electrochemical sensor according to the present disclosure in front elevational view (FIG. 3A), side elevation view (FIG. 3B), and bottom planar view (FIG. 3C).
Figure 3B:
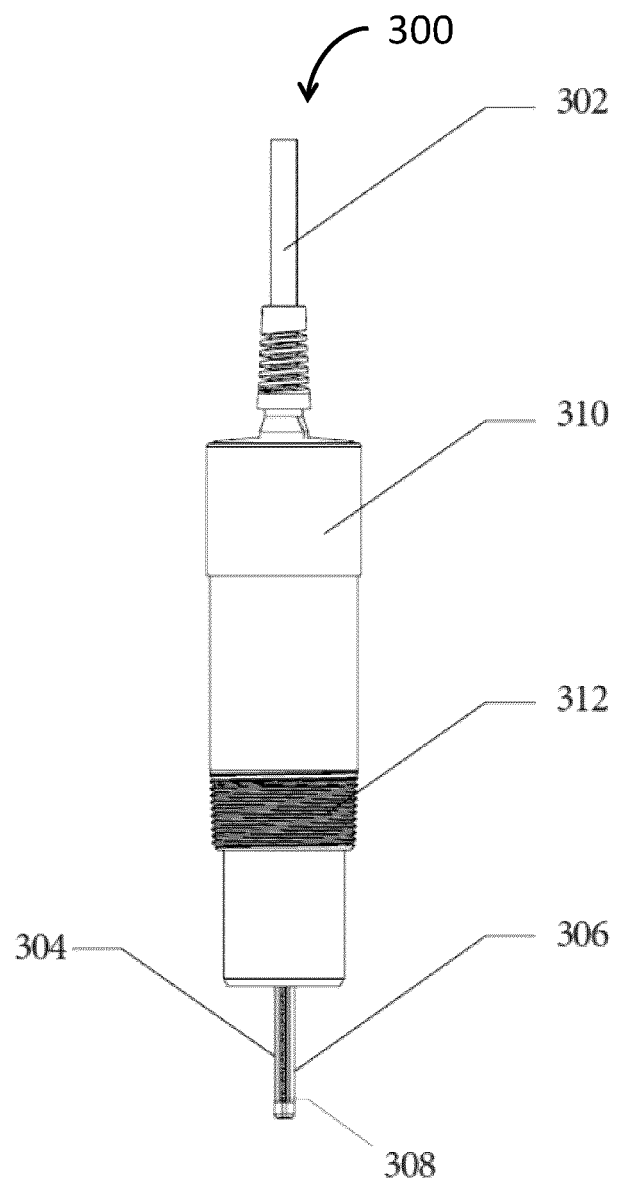
Figure 3C:
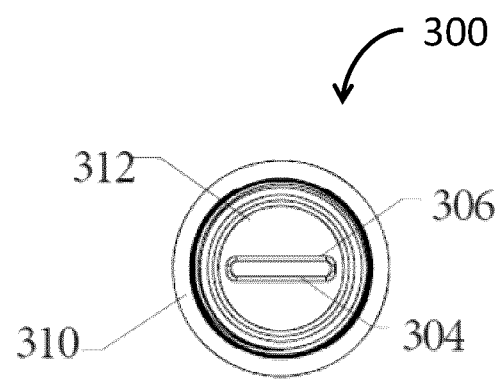

A further exemplary bio-electrochemical sensor configuration is shown in FIGS. 3A-C from various perspectives. The sensor (300), comprises a power and data cable (302) for connecting the sensor to a power source and electrical output analyzer (not shown); an electrode pair comprising a cathode (306) and anode (304), wherein the anode (304) is in electrical communication with exo-electrogenic bacteria (not shown), coupled to a bio support (308), for receiving electrons therefrom; a sealed probe body (310) for housing the electrode pair; and an installation thread (312) for connecting the sensor to various fittings. As more clearly depicted in FIG. 3B, the cathode (306) and the anode (304) are configured in parallel, and at least a portion of the anode (304) overlaps with at least a portion of the cathode (306). In some examples, the distance between the overlapping portions is about 3 mm.

The presently disclosed systems, methods and sensors may be used to increase performance of wastewater treatment processes, increase cost-efficiency of wastewater treatment processes, increase reliability of waste treatment processes, or a combination thereof, by, for example, monitoring and predicting conditions that are suitable for nitrification, denitrification and phosphorous accumulation to take place and to control the level of organic carbon compounds being added to the wastewater treatment system.

References to other documents are made throughout this disclosure. Such documents are incorporated herein by reference in their entirety.

EXAMPLES

Example 1—Decrease in Activity Over Time Correlates with Decreasing BOD Concentration in the Wastewater In this experiment, bio-electrochemical sensors according to the present disclosure were run as batch reactors with regular flushing of the probe with buffered solution between each test, and the response of the bio-electrochemical sensor was recorded until the response fell to background levels (deemed to be caused by endogenous respiration). After this period, a feed synthetic wastewater was put in the cup to sustain the microbial community until another sample was prepared.

Figure 4:
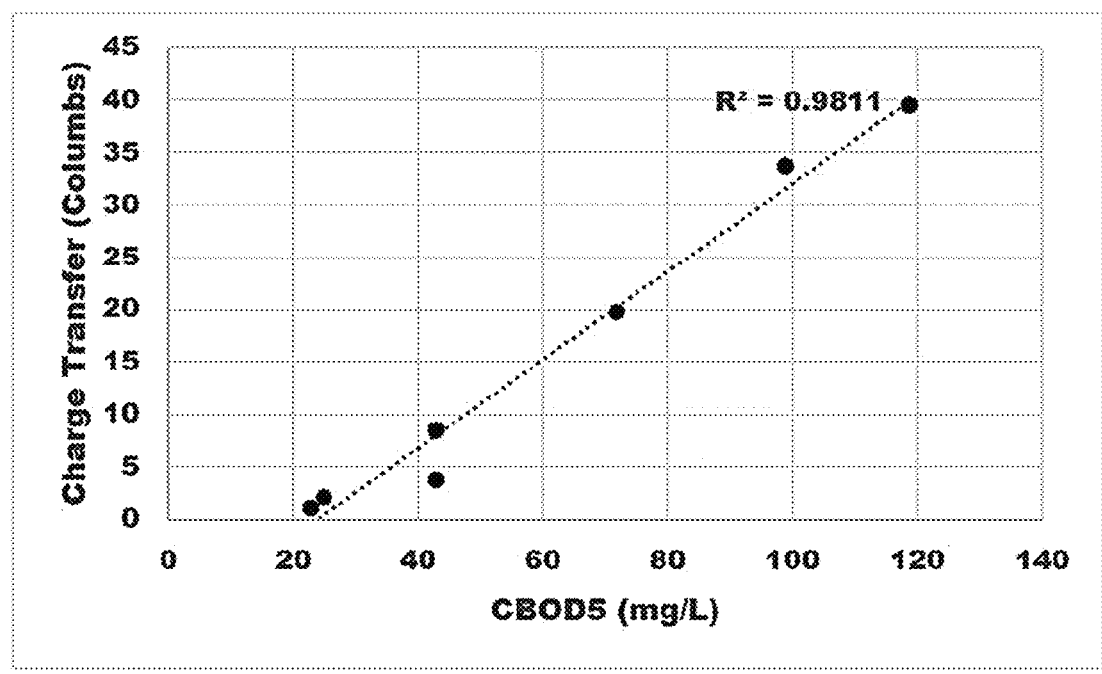
FIG. 4 is a graph illustrating a bio-electrogenic response to defined concentrations of acetic acid (20-120 mg/L) that was added to a wastewater treatment system (additions signified with dots). The bio-electrogenic response output with varying acetic acid concentrations provides a clear correlation at end of pipe target ranges.

Bench-scale testing was performed on: (i) a synthetic wastewater with sodium acetate as a source of Carbonaceous Biochemical Oxygen Demand ($CBOD_5$), and (ii) domestic wastewater samples collected directly from a septic settling tank at Dalhousie's BEEC (Bio-Environmental Engineering Centre). The wastewater at the collection site had already undergone settling and was low in solids (<25 mg/L). A range of $CBOD_5$ concentration was created from the domestic wastewater samples by diluting samples in phosphorous buffer with additions of minerals and nutrients. Two metrics were used to create a relationship with $CBOD_5$: (i) total charge transferred (integrated current) and (ii) max current. A strong linear relationship between charge transferred and $CBOD_5$ concentration was found (see FIG. 4).

Figure 5:
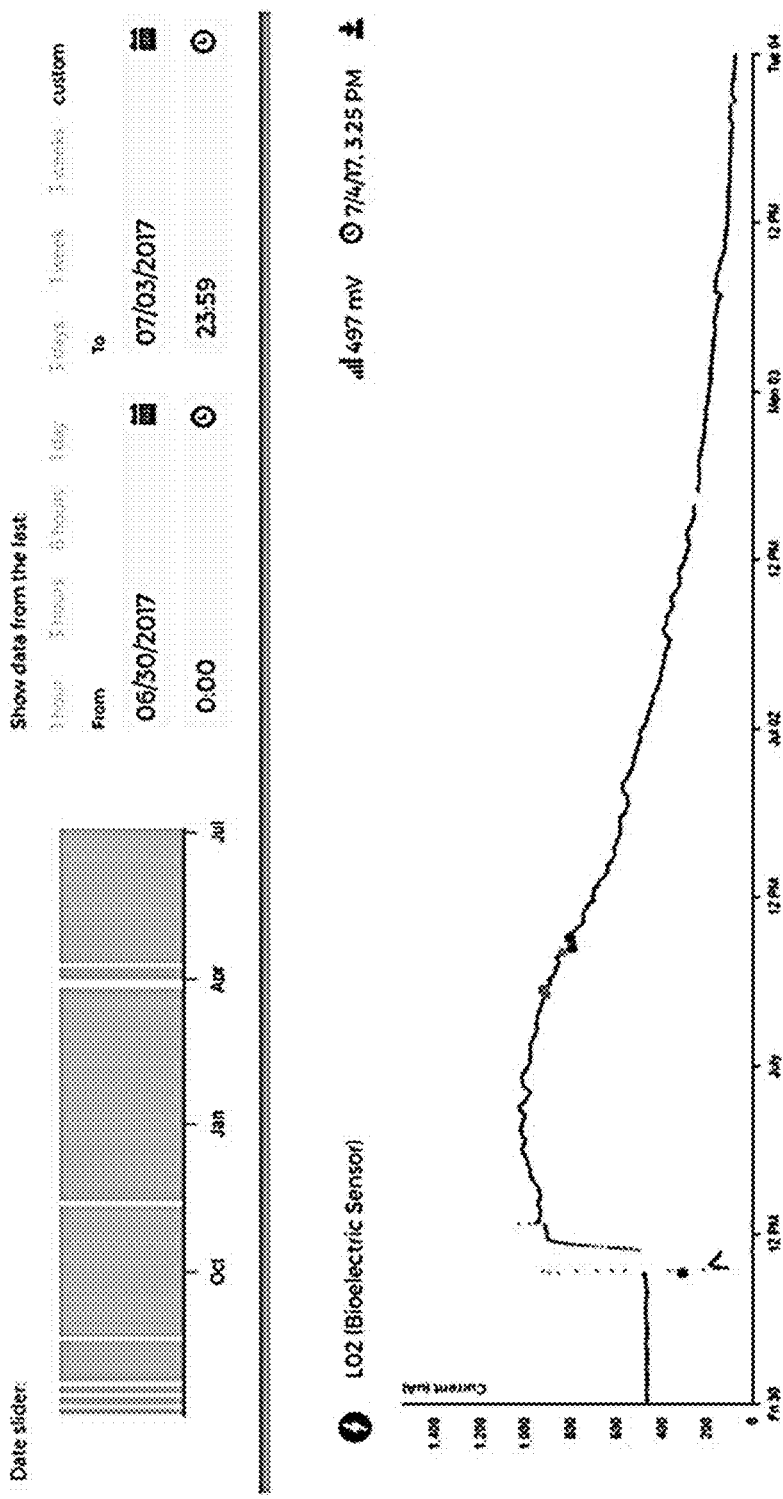
FIG. 5 is a graph illustrating bio-electrogenic output from an exemplary bio-electrochemical sensor according to the present disclosure showing decrease in activity over time that correlates with decreasing BOD concentration in the wastewater.

The results of this work were encouraging for the potential of bio-electrochemical systems, methods, and sensors according to the present disclosure to act as real-time tools for monitoring $CBOD_5$ concentrations in wastewater streams. The data shows a strong correlation between both the instantaneous current and charge transfer with $CBOD_5$. FIG. 5 graphically depicts the impact of batch-state operation on the bio-electrochemical output and how it correlated with decreasing BOD concentrations in solution.

Example 2—Use of Sensors in a Wastewater Treatment System or Plant

A SENTRY system, that included SENTRY bio-electrochemical sensors according to the present disclosure, were installed at 3 different tie-in locations that were connected to two separate communications devices, was installed on Jun. 14, 2018 at a functional wastewater treatment system or plant (WWTP). The WWTP consisted of primary treatment (screening, grit removal and equalization), secondary treatment (anoxic and aerobic treatment), and anaerobic digestion for solids management.

The WWTP was originally designed to treat nitrate down below a 10 mg/L effluent limit; however, due to increased ammonia concentrations in influent on Wednesdays and Thursdays, the WWTP was trialing addition of supplemental bio-available carbon to anoxic treatment tanks to provide sufficient carbon for a denitrification process. The SENTRY systems were installed at two locations, in the primary clarifier effluent and the anoxic tanks. The goal for the sensors of the primary clarifier installation was to serve as an estimate on the influent biologically available carbon entering into the WWTP. It was considered that this information combined with data on influent ammonia concentrations may be used to identify time periods where a ratio of influent wastewater bioavailable carbon concentration/ammonia is low, which may assist operators when determining a dosing schedule. The goal for the sensors installed in the anoxic tank was to provide feedback on microbial activity in the anoxic tanks, to better understand what affect bio-available carbon was having, and to understand time frames where the biology in the anoxic tank were carbon limited, and control conditions in the bioreactor to have optimized concentrations of bio-available carbon.

Two separate control/communication panels were installed, and three total SENTRY sensors were installed. The first panel was installed near the primary clarifier, with the sensor installed upstream of the effluent weirs of the primary clarifier, about a foot deep, just downstream of where the flights dive and 10 feet upstream of the scum beach. It was installed next to an influent ammonia sensor to the WWTP.

Figure 6:
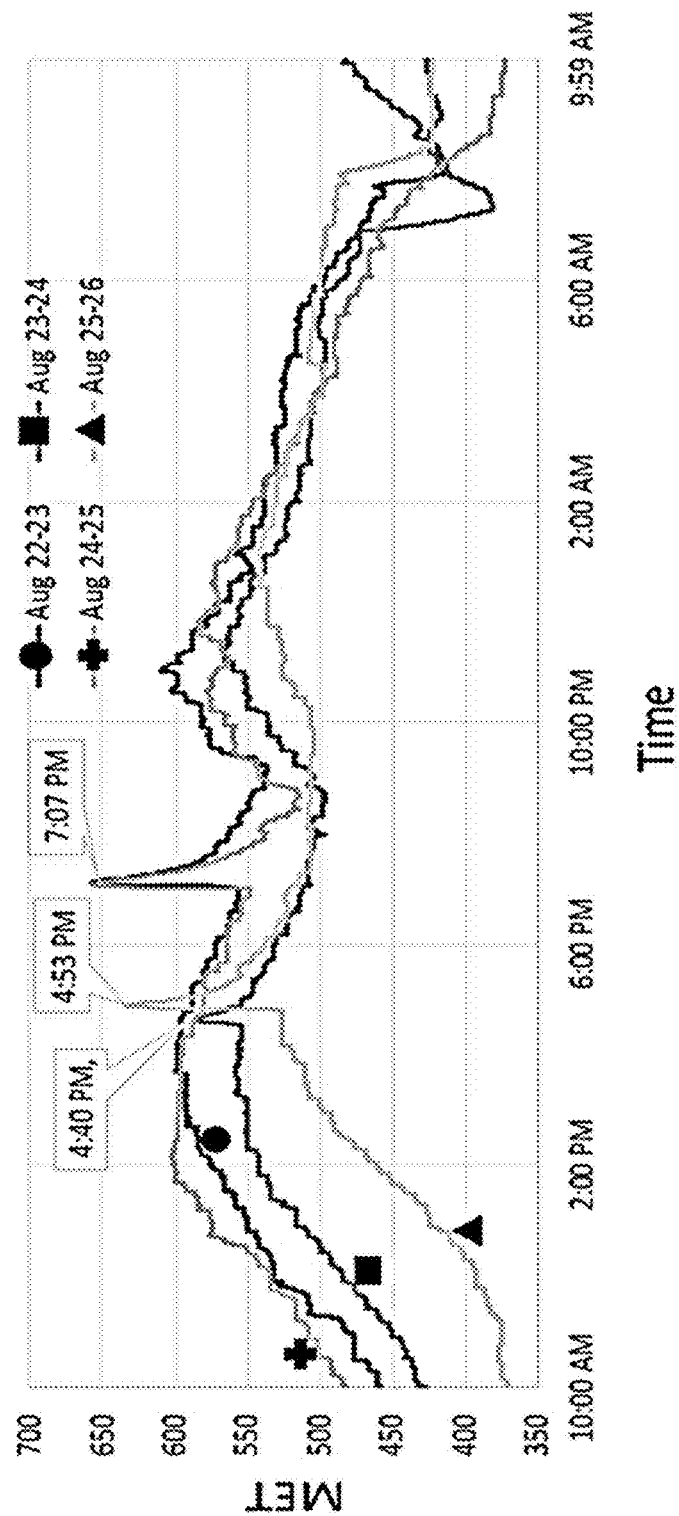
FIG. 6 is a graph illustrating bio-electrogenic output from a sensor (SENSOR 1) picking up changes in bio-available carbon coming into a wastewater treatment system or plant (WWTP) and entering a nitrogen removal component of the WWTP.
Figure 7:
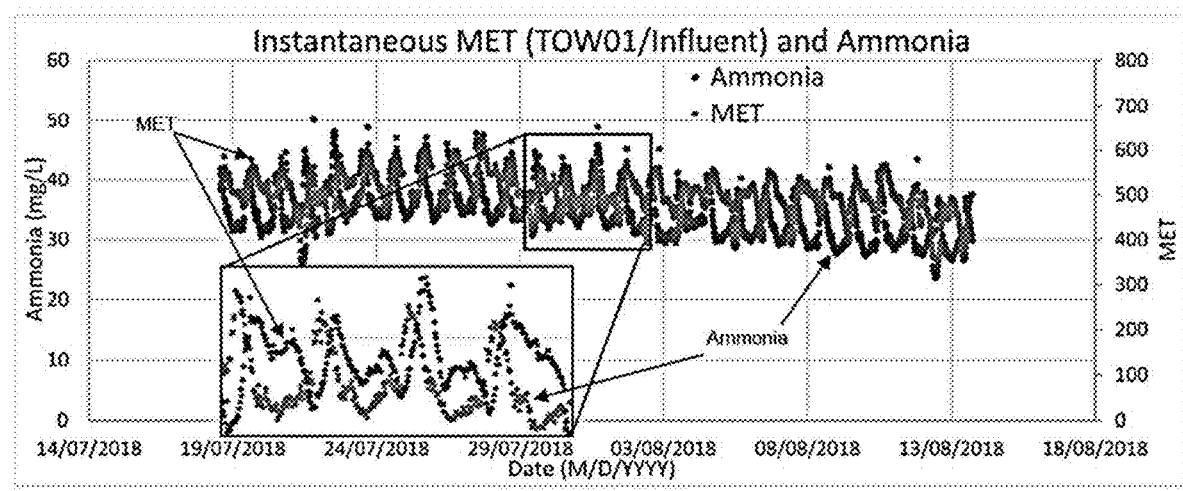
FIG. 7 is a graph illustrating that SENSOR 1 was able to characterize a change in biological available carbon with respect to ammonia concentration, a ratio critical for nitrogen and phosphorous removal efforts.

SENSOR 1: The primary clarifier sensor was able to pick up changes in the bio-available carbon coming into the WWTP. The variation throughout the days and weeks was valuable to the operators, as it allowed them to understand how the influent wastewater conditions were not consistent and changed with obvious daily and weekly patterns emerging, and were able to plan their carbon addition during the insufficient periods. The sensor was also able to pick up the impact that the anaerobic digestion filtrate was having on this available carbon. This anaerobic digestion filtrate was assumed to be providing an insignificant organic load to the overall system, however, the sensor was able to characterize that this was not the case, and that the timing of that dosing needed to be reconsidered. See FIGS. 6 and 7.

SENSOR 2 and SENSOR 3: The sensors in the anoxic tank were originally installed in two different anoxic tanks (parallel tanks), however they were eventually moved to the same reactor to provide further information. These sensors provided real-time insights to the WWTP operators on the bio-available carbon present in the anoxic tank locations. Additional carbon was added into this tank and measurements recorded from SENSOR 2 and SENSOR 3 could be used to better understand the dosing requirements.

Figure 8:
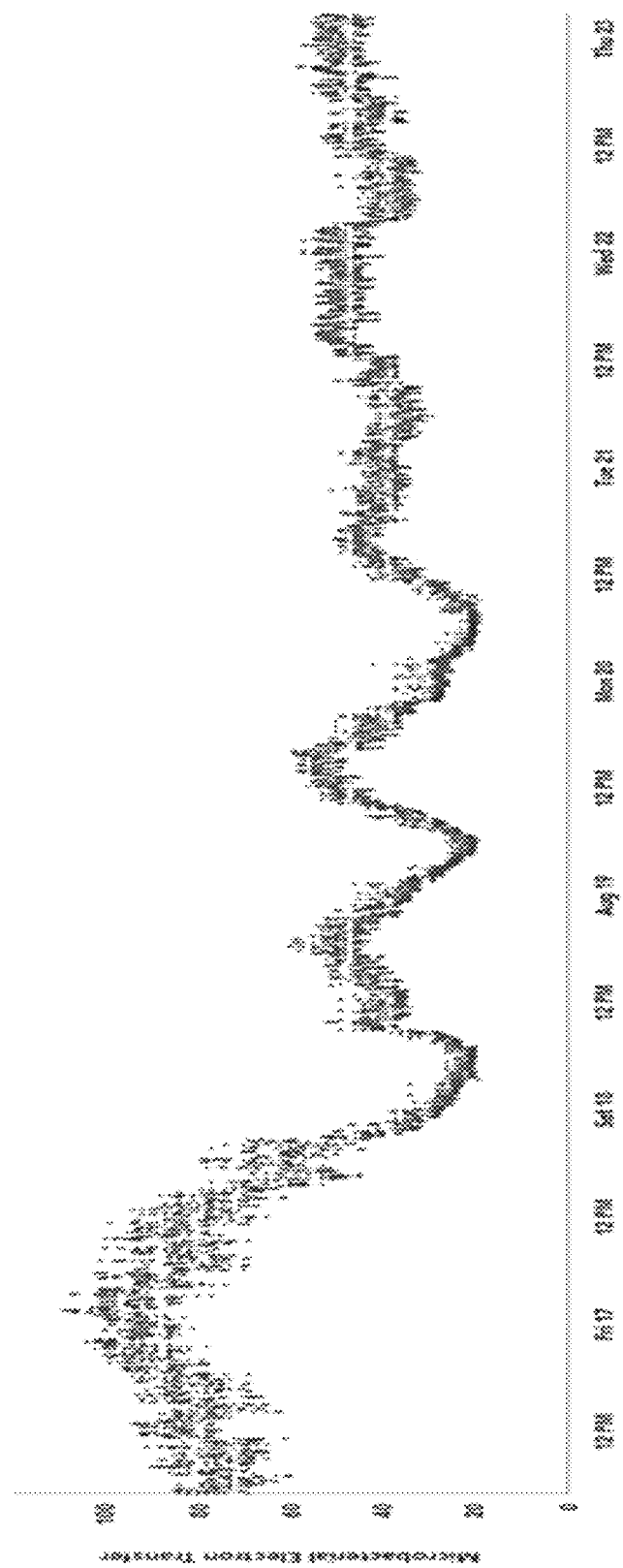
FIG. 8 is a graph illustrating that SENSOR 2 and SENSOR 3 located in an anoxic tank of the WWTP was able to show shifts and changes in levels of biological carbon available in the anoxic tank, showing impacts both around the time of supplemental biologically available carbon addition, as well as during normal operation.

These sensors, located in denitrification reactor, were demonstrated to pick up fluctuating organic carbon concentrations in the system. Daily and weekly trends were analyzed as well as any correlations to loading of carbon to the system. Location of the sensors was important and the sensors could be used to track where carbon became limiting in a reactor. This was particularly true if the reactor was operated in a plug-flow, had a series of steps, or had a potential for hydraulic dead zones. The data recorded by these sensors demonstrated the fluctuating output and presented when the biology of the exo-electrogenic bacteria have the ability for higher and lower microbe-electron transfer. See FIG. 8.

Figure 9:
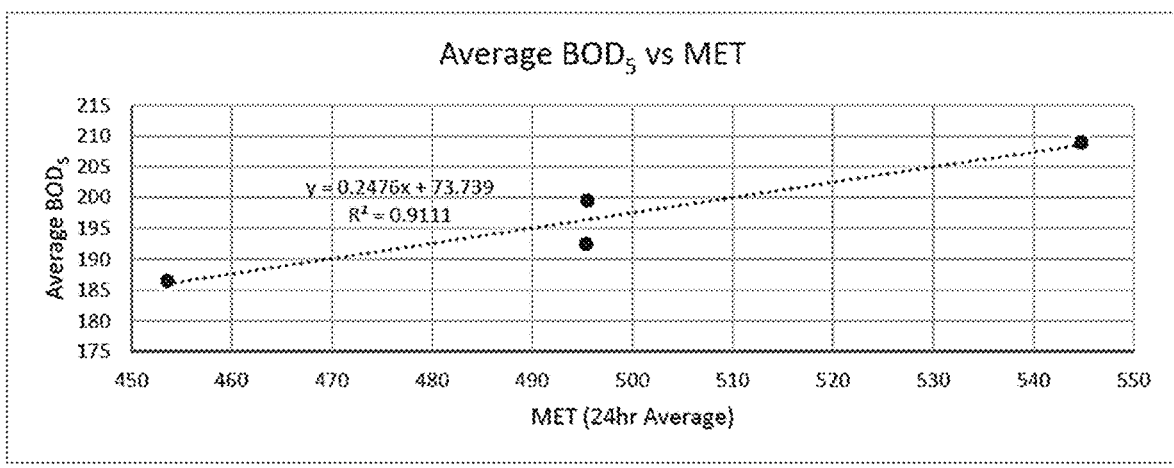
FIG. 9 is a graph illustrating a correlation between SENTRY Sensor MET and measured $BOD_5$.

The 24-hour composite sample results provided (see FIG. 9) were compared to a 24 hour average MET (Microbial Electron Transfer) signal, the reading or metric used when measuring the output from the sensor, during those collection periods. Results from the raw influent and a sample point just after the primary clarifiers were used. The install location of the sensor was between the two composite sample locations. More particularly, Sensor 1 was positioned in between two BOD samplers. As such, the output (MET) from Sensor 1 was correlated to the BOD measurements recorded from the two sample locations. The average of the two BOD composite samples was graphed as well, with a good $R^2$ value (0.911). See FIG. 9.

These correlations were used to provide an estimate of the available BOD concentrations during this test period. This data was used to fill in the gaps associated with only having a composite sample (1 test point per day, the results obtained from Sensor 1), and to see the variance of bioavailable carbon in real-time. This provided insight into daily and weekly patterns and correlations to carbon loading.

Example 3—Preparation of Bio-Electrochemical Sensor

Preparing a bio-electrochemical sensor described herein, and specifically the exo-electrogenic microbial communities thereof, involved the following steps:

1. Collecting a seed sample from an already operating bio-electrochemical sensor according to the present disclosure (preferred); or alternatively, from a wastewater or environmental source.

2. Mixing up a liquid feed according to Table 1 in a preferred concentration (recommendation is 25×1 L); and measuring out the required masses into a 1 L container, filling the container to the 1 L mark, and mixing thoroughly so as to introduce oxygen.

3. Adding to a feed mixing vessel (measuring cup) the following: 40 mL of 25× feed solution per Liter; the seed (if starting from previous reactors, a 1 in 5 dilution was used for optimal start-up times. (200 ml/1 Liter)); and topping up with desired volume of water.

4. Filling all inoculation cups with the seeded feed water, making sure to leave room for displacement when the sensor was added; and, mixing thoroughly so as to introduce oxygen.

5. Monitoring cells for biological activity for 48 hours; at this time the cells were emptied and again re-fed with an oxygenated seeded feed water.

6. Continuing the feeding cycle of the inoculation process over a 14-day period, at which time the exo-electrogenic microbial biofilm were deemed suitable for installation.

TABLE 1

Adapted synthetic wastewater recipe (Peel & Nyberg 1989) used as the inoculation and feed for the SENTRY inoculation cells with the addition of sodium acetate and making a 25 × 1 L stock solution.

| Component | Diluted Concentration (mg/l) | 25 × Mass (mg) 1 L |
|---|---|---|
| $NaHCO_3$ | 525 | 13125 |
| Casein hydrolysate | 525 | 13125 |
| Meat extract | 350 | 8750 |
| Urea | 90 | 2250 |
| NaCl | 21 | 525 |
| $CaCl_2$ | 10.1 | 252.5 |
| $mgSO4•7 H_2 0$ | 7 | 175 |
| Sodium acetate | 250 | 6250 |

The foregoing procedure did not involve any aspects of sparging wastewater streams for the exclusion of oxygen from the inoculation process. Original wastewater seed samples were collected typically from aerated zones of a wastewater treatment plant. During cell inoculation, there was no sparging of feed wastewater or of seed inoculum. Furthermore, an air-tight seal on the sensor inoculation cells was not required.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A method of monitoring one or more organic carbon compounds in a wastewater treatment system, the method comprising:
    applying power to a bio-electrochemical sensor comprising an anode electrode and a cathode electrode, the cathode being in electrical communication with a non-dioxygen terminal acceptor, wherein each of the anode and cathode electrodes is within one chamber of the treatment system;
    measuring an electrical output of the bio-electrochemical sensor and correlating the electrical output with metabolic activity of exo-electrogenic bacteria present in the chamber; and
    correlating the electrical output with the one or more organic carbon compounds in the wastewater treatment system,
    wherein the wastewater treatment system is an anaerobic digestion system, an anoxic digestion system, a denitrifying system, or a phosphorous removal system.

2. The method of claim 1, wherein the one chamber is a denitrifying tank or a phosphorous removal tank.

3. The method of claim 1, wherein the one chamber comprises oxygen at a concentration of about 2 mg/L and: (i) nitrate at a concentration from about 5 mg/L to about 100 mg/L; (ii) bio-available carbon at a concentration from 0 mg/L to about 100 mg/L; or a combination of (i) and (ii).

4. The method of claim 1, wherein the one chamber comprises nitrate at a concentration from about 5 mg/L to about 100 mg/L; bio-available carbon at a concentration from 0 mg/L to about 100 mg/L; oxygen at a concentration of about 2 mg/L; or any combination thereof.

5. The method of claim 3, wherein the one or more organic carbon compounds comprises a volatile fatty acid, an organic acid, a complex organic compound, acetic acid, propionic acid, butyric acids, or any combination thereof.

6. The method of claim 3 for controlling delivery of one or more organic carbon compounds in the wastewater treatment system, comprising:
    delivering one or more organic carbon compounds into the wastewater treatment system;
    monitoring a change in the electrical output in response to the one or more organic carbon compounds; and
    adjusting the delivery of one or more organic carbon compounds in response to a change in the electrical output.

7. The method of claim 6, wherein the adjusting step comprises real time adjustments in the delivery of the one or more organic carbon compounds, wherein the delivery of the one or more organic carbon compounds is adjusted in response to a change in electrical output beyond a threshold.

8. The method of claim 6 for controlling a nitrogen removal process and/or a phosphorous removal process in a wastewater treatment system.

9. The method of claim 7, wherein the threshold represents a change in a ratio of the value representing the amount of the one or more organic carbon compounds to a value representing the amount of nitrogen and/or phosphorous in the wastewater treatment system, and wherein the delivery of the one or more organic carbon compounds initiates, adjusts, maintains, or stops a nitrification process, a simultaneous nitrification and denitrification process, a denitrification process, and/or a carbon addition process.

10. The method of claim 9, wherein:
    the ratio of the value representing the amount of the one or more organic carbon compounds to a value representing the amount of nitrogen is: about 0:1; about 1:1, about 2:1; about 3:1; about 4:1; about 5:1; about 6:1; about 7:1; about 8:1; about 9:1; or about 10:1, or greater than about 4:1; greater than about 5:1; greater than about 6:1; greater than about 7:1; greater than about 8:1; greater than about 9:1; greater than about 10:1; greater than about 11:1; or greater than about 12:1; and
    the ratio of the value representing the amount of the one or more organic carbon compounds to a value representing the amount of the phosphorous is less than about 10:1; less than about 15:1; less than about 20:1; less than about 25:1; less than about 30:1; less than about 35:1; less than about 40:1; less than about 45:1; or less than about 50:1.

11. The method of claim 6 further comprising adjusting delivery of nitrogen and/or phosphorous to the wastewater treatment system in response to the change in the electrical output.

12. The method of claim 1 wherein the one chamber is a chamber within a reactor of the wastewater treatment system.

* * * * *